(12) United States Patent
Sergio et al.

(10) Patent No.: US 6,521,180 B2
(45) Date of Patent: Feb. 18, 2003

(54) METHOD OF STERILIZATION

(75) Inventors: Roberto M. Sergio, Jenkintown, PA (US); Winfield Wood, Jr., Gywnedd, PA (US)

(73) Assignee: Sermed Industries, Inc., Abington, PA (US)

( * ) Notice: Subject to any disclaimer, the term of this patent is extended or adjusted under 35 U.S.C. 154(b) by 0 days.

(21) Appl. No.: 09/998,580

(22) Filed: Nov. 16, 2001

(65) Prior Publication Data

US 2002/0037236 A1 Mar. 28, 2002

Related U.S. Application Data

(63) Continuation-in-part of application No. 09/425,261, filed on Oct. 22, 1999, now Pat. No. 6,379,614.
(60) Provisional application No. 60/249,595, filed on Nov. 17, 2000, provisional application No. 60/105,115, filed on Oct. 22, 1998, provisional application No. 60/105,225, filed on Oct. 22, 1998, and provisional application No. 60/105,221, filed on Oct. 22, 1998.

(51) Int. Cl.[7] ................................................ A61L 2/00
(52) U.S. Cl. ........................... 422/28; 422/32; 422/33; 422/109; 422/116
(58) Field of Search ............................ 422/28, 32, 33, 422/3, 109, 116, 292, 293

(56) References Cited

U.S. PATENT DOCUMENTS 4,752,444 A   6/1988   Bowen et al.
5,008,079 A   4/1991   Wutzler et al.
5,037,623 A   8/1991   Schneider et al.
5,077,008 A   12/1991  Kralovic et al.
5,225,160 A   7/1993   Sanford et al.
5,348,711 A   9/1994   Johnson et al.
6,379,614 B1 * 4/2002  Sergio et al. ............... 422/109

FOREIGN PATENT DOCUMENTS

DE           3239549 A1    4/1984

* cited by examiner

Primary Examiner—Krisanne Thornton
(74) Attorney, Agent, or Firm—Akin, Gump, Strauss, Hauer & Feld, L.L.P.

(57) ABSTRACT

A method of sterilizing an instrument having an exterior and a proximal end in a chamber of a sterilizing apparatus, the method including the following steps: washing the instrument with a rinse fluid; removing bio-burden from the instrument with a bio-burden removing fluid; stabilizing a sterilization temperature at which sterilization of the instrument occurs; sterilizing the instrument; a first rinsing of the instrument with the rinse fluid; and a first drying of the instrument. The sterilizing step includes: applying to the instrument a first application of a sterilizing fluid at a first predetermined flow rate and applying to the instrument a second application of the sterilizing fluid at a second predetermined flow rate. The first application includes a first predetermined sequence of pulses of the sterilizing fluid and a driving fluid. The second application includes a plurality of pulses of the sterilizing fluid.

12 Claims, 8 Drawing Sheets

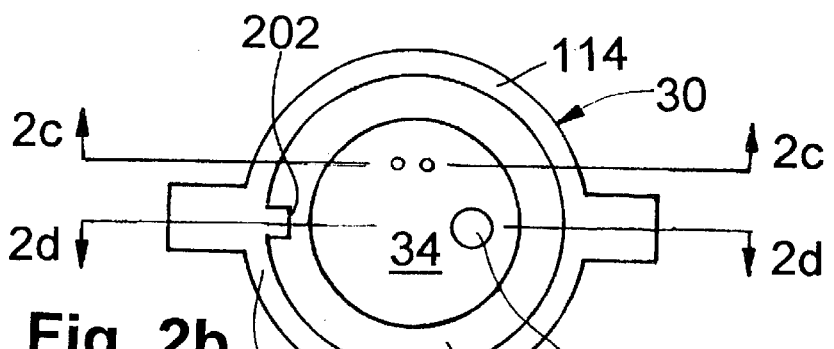
Fig. 2b
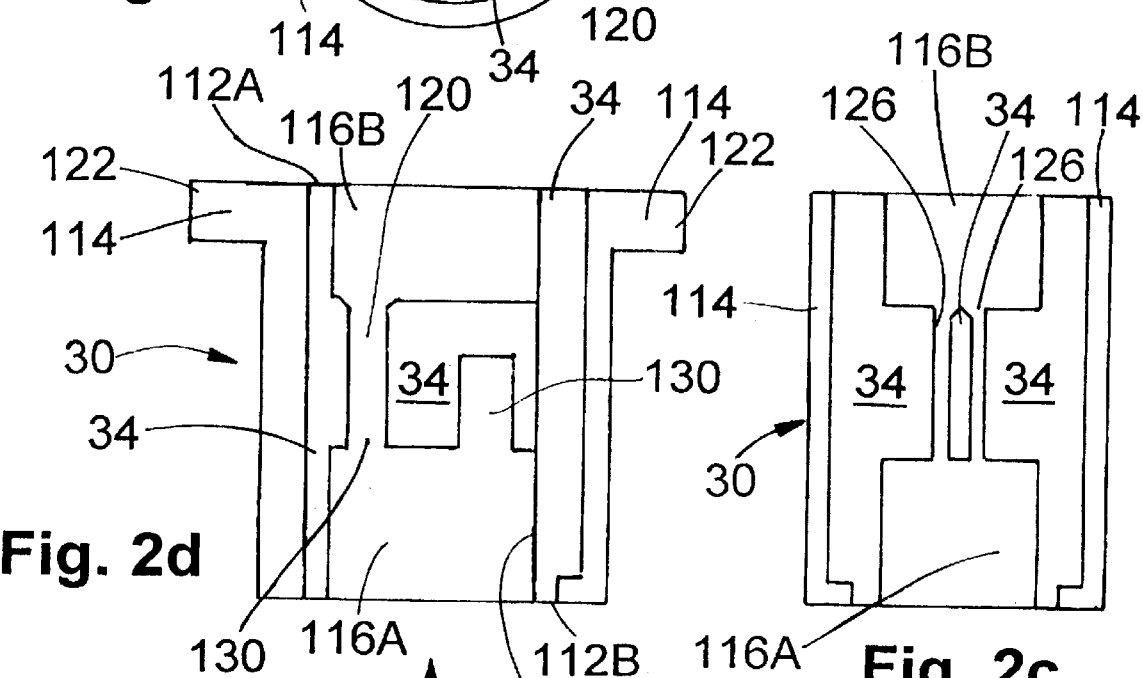
Fig. 2d
Fig. 2c
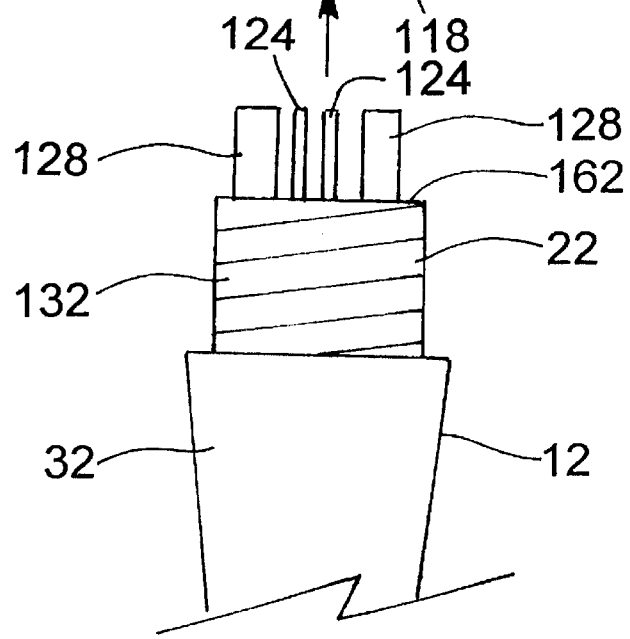
Fig. 2a

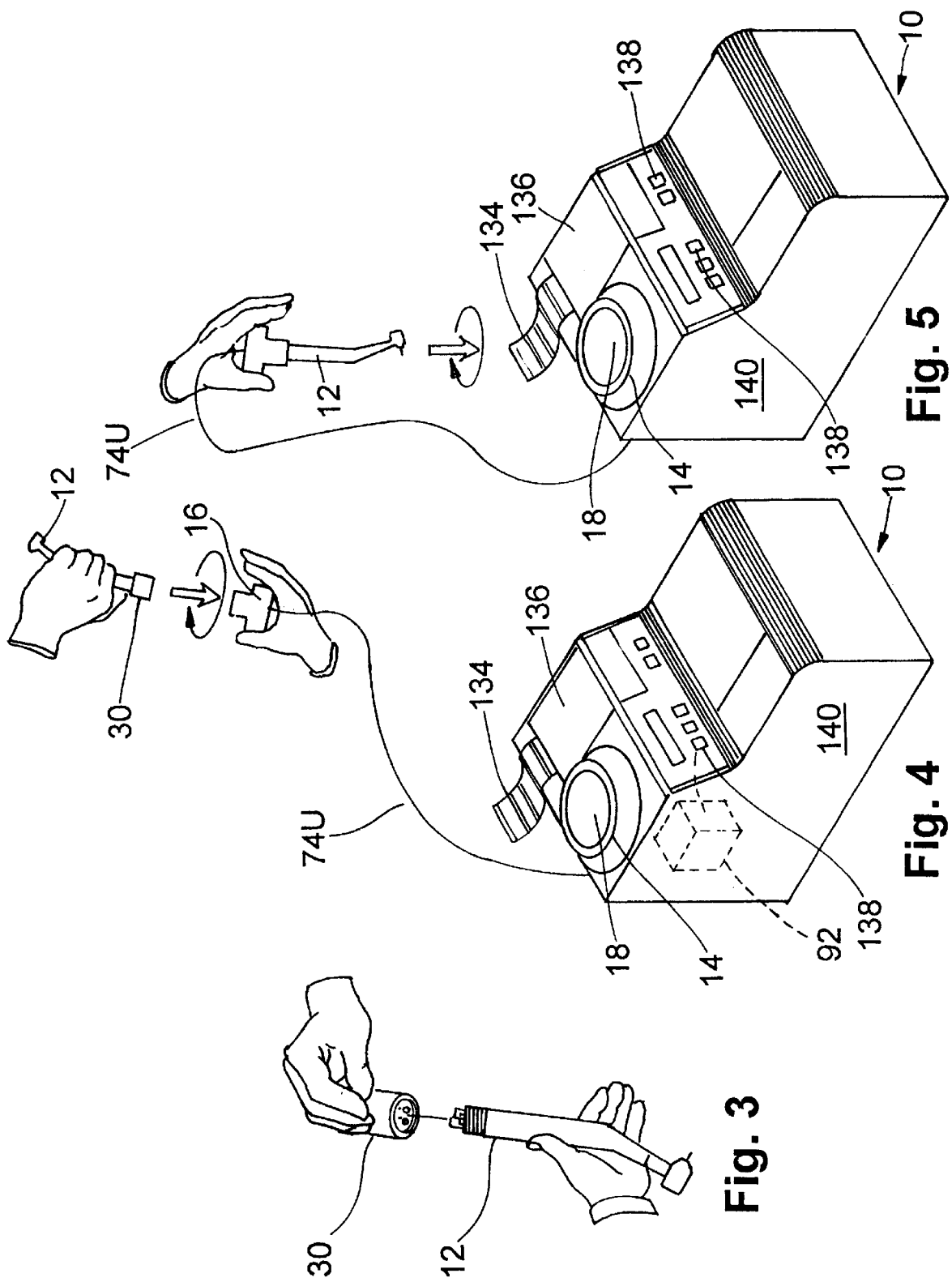

METHOD OF STERILIZATION

CROSS-REFERENCE TO RELATED APPLICATIONS

This application is a continuation in part of U.S. patent application Ser. No. 09/425,261 entitled "Apparatus and Method for Sterilizing an Instrument at Substantially Room Temperature," filed Oct. 22, 1999, and which is now U.S. Pat. No. 6,379,614 which is hereby incorporated by reference herein in its entirety and additionally claims the benefit of Provisional Application No. 60/249,595 entitled "Method of Sterilization," filed Nov. 17, 2000.

U.S. patent application Ser. No. 09/425,261 claims priority from: U.S. Provisional Patent Application No. 60/105,115 entitled, "Method and Apparatus for the Sterilization of Dental Handpieces at Room Temperature" filed Oct. 22, 1998, which is hereby incorporated by reference herein in its entirety; U.S. Provisional Patent Application No. 60/105,225 entitled, "Apparatus for the Sterilization of Threaded Areas of Dental Handpieces " filed Oct. 22, 1998, which is hereby incorporated by reference herein in its entirety; and from U.S. Provisional Patent Application No. 60/105,221 entitled, "Cartridge Assembly for Sterilant Containment " filed Oct. 22, 1998, and is hereby incorporated by reference herein in its entirety.

BACKGROUND OF THE INVENTION

The present invention relates to the sterilization of thermosensitive instruments and, more specifically, to a method for sterilizing thermosensitive instruments while preferably exposing the instruments to substantially room temperatures during the sterilization process.

Current methods for sterilizing instruments include using steam autoclaves, using ethylene oxide, or using irradiation. While these methods are effective for sterilizing instruments, none of these methods are suitable for performing instrument sterilization at a patient side location while exposing the instrument to substantially room temperatures during the sterilization process.

Steam autoclaves operate at temperatures ranging between two hundred-forty degrees Fahrenheit and two hundred seventy-five degrees Fahrenheit for extended periods of time. The high temperatures used by steam autoclaves have been known to damage thermosensitive instruments, such as the turbines of a dental handpiece, and tend to reduce the useful life of the thermosensitive instruments. This results in the associated medical instruments requiring more frequent and expensive refurbishing.

Ethylene oxide is a carcinogenic, flammable, and highly toxic substance. Expensive ventilation systems are required before the discharge resulting from the ethylene oxide sterilization process is released to the atmosphere. Thus, the use of ethylene oxide raises safety issues with regard to the sterilization of instruments at a patient-side location. Problematic environmental issues are also associated with the use of ethylene oxide.

The use of irradiation for sterilization is not a practical solution for normal patient-side applications. Irradiation sterilization requires large and expensive installations and protective measures which makes irradiation sterilization unsuitable for use at a patient-side location.

Currently, the pre-cleaning of soiled medical instruments prior to the exposure of the instrument to the actual sterilizing heat, chemicals, or radiation depends on manual cleaning which is performed by medical personnel. The reliance on medical personnel for the manual cleaning of instruments increases the chance of inadequate cleaning due to human error or due to the omission of pre-cleaning all together.

Chemical sterilization can be used to sterilize instruments at room temperature, but it is difficult and hazardous to manually perform. One method of overcoming the difficulties of manual sterilization is to automate the process. However, one problem with automating a chemical sterilizing process is ensuring that the instrument is sterilized according to the U.S. Food and Drug Administration ("FDA") standards with all of the pathogens and spores killed and removed from every surface of the instrument being sterilized. If the chemicals used to sterilize the instrument are not correctly applied to the instrument, the instrument will not be sterilized as defined by the FDA. The FDA requires that a sterilizer have a STERILITY ASSURANCE LEVEL (SAL) of $10^{-6}$. The SAL number represents the probability of a non-sterile unit (e.g., a contaminating micro organism or the like) surviving the sterilization process. Thus, a sterilizing apparatus having a SAL rating of $10^{-6}$ is capable of sterilizing an instrument bearing one million contaminating units with no more than one non-sterile unit surviving the process. The difficulty in meeting current FDA standards is exacerbated when sterilizing dental handpieces or other instruments having lumens or internal passages.

What is needed, but so far not provided in the sterilizing art, is method of applying chemicals to dental handpieces, and other instruments having internal passages, which results in the elimination or destruction of life, including micro organisms, on the dental handpiece at least in accordance with a STERILITY ASSURANCE RATING of $10^{-6}$ as currently set forth by the FDA.

BRIEF SUMMARY OF THE INVENTION

One aspect of the present invention is a method of sterilizing an instrument in a chamber of a sterilizing apparatus. The instrument has an exterior and a proximal end. The method comprising applying to the instrument a first application of a sterilizing fluid at a first predetermined flow rate and applying to the instrument a second application of the sterilizing fluid at a second predetermined flow rate. The first application comprises a first predetermined sequence of pulses of the sterilizing fluid and a driving fluid. The second application comprises a plurality of pulses of the sterilizing fluid.

Another aspect of the present invention is a method of sterilizing an instrument in a chamber of a sterilizing apparatus. The instrument has an exterior and a proximal end. The method comprises: washing the instrument with a rinse fluid; removing bio-burden from the instrument with a bio-burden removing fluid; stabilizing a sterilization temperature at which sterilization of the instrument occurs; sterilizing the instrument; a first rinsing of the instrument with the rinse fluid; and a first drying of the instrument. The sterilizing step comprises: applying to the instrument a first application of a sterilizing fluid at a first predetermined flow rate and applying to the instrument a second application of the sterilizing fluid at a second predetermined flow rate. The first application comprises a first predetermined sequence of pulses of the sterilizing fluid and a driving fluid. The second application comprises a plurality of pulses of the sterilizing fluid Still another aspect of the present invention is a method of sterilizing an instrument in a chamber of a sterilizing apparatus. The instrument has an exterior and a proximal end. The method comprises: washing the instrument with a rinse fluid; a first drying of the instrument; removing bio-burden from the instrument with a bio-burden removing fluid; a first rinsing of the instrument with the rinse fluid; a second drying of the instrument; stabilizing a sterilization temperature at which sterilization of the instrument occurs; sterilizing the instrument; a second rinsing of the instrument with the rinse fluid; and a third drying of the instrument. The sterilizing step comprises applying to the instrument a first application of a sterilizing fluid at a first predetermined flow rate and applying to the instrument a second application of the sterilizing fluid at a second predetermined flow rate. The first application comprises a first predetermined sequence of pulses comprising the sterilizing fluid and a driving fluid. The second application comprises a plurality of pulses of the sterilizing fluid.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown. In the drawings:

The detailed description of the preferred embodiment of the method of the present invention will be better understood when read in conjunction with the appended drawings. For the purpose of describing one type of sterilizing apparatus that can be used with the method of the present invention, there is shown in the drawings an exemplary apparatus suitable for performing the method of the present invention. The drawings also include charts detailing a preferred embodiment of the method of the present invention. It is understood that the method of the present invention can vary from the illustrated charts without departing from the scope of the present invention. In the drawings:

FIG. 2*a* is an enlarged partial view of a proximal end of the instrument shown in FIG. 1;

FIG. 2*b* is an enlarged top planar view of a coupler of FIG. 1;

FIG. 2*c* is an enlarged cross-sectional view of the coupler of FIG. 2*b* as taken along the lines 2*c*—2*c* of FIG. 2*b*;

FIG. 2*d* is an enlarged cross-sectional view of the coupler of FIG. 2*b* as taken along the lines 2*d*—2*d* of FIG. 2*b*;

FIG. 3 is a perspective view of the instrument of FIG. 1 being attached to the coupler of FIGS. 2*c* and 2*d*;

FIG. 4 is a perspective view of the apparatus of FIG. 1 illustrating the insertion of the combination of the instrument and the coupler of FIG. 3 into a lid, which includes a coupler housing, of the apparatus of FIG. 1;

FIG. 5 is a perspective view showing the insertion of the instrument, which is attached to the lid of the chamber of FIG. 1, into the apparatus;

DETAILED DESCRIPTION OF THE INVENTION

Figure 1:
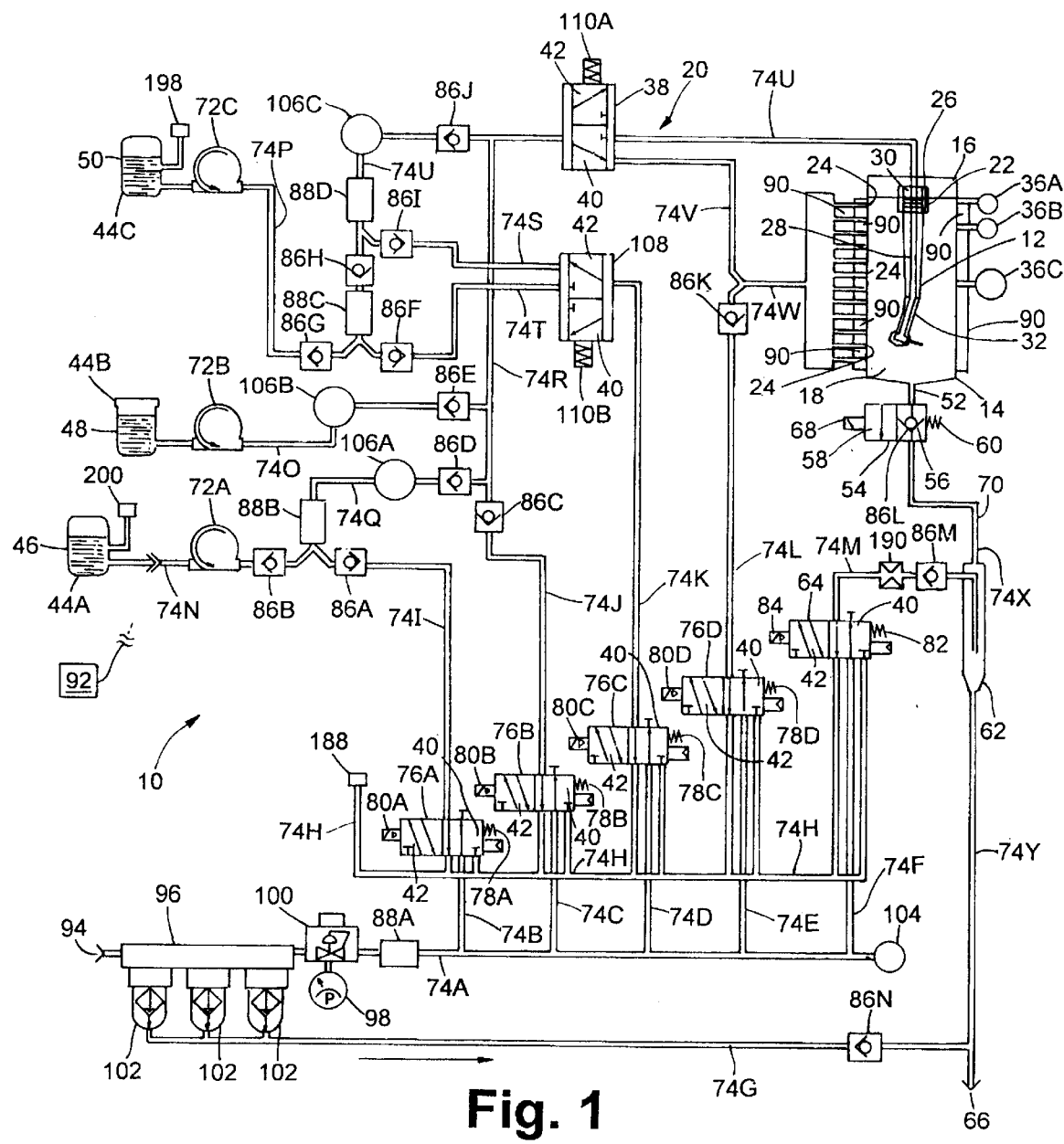
FIG. 1 is a schematic of one possible apparatus for sterilizing an instrument which can be used with the preferred method of the present invention.

Certain terminology is used in the following description for convenience only and is not limiting. The words "right," "left," "lower" and "upper" designate directions in the drawings to which reference is made. The words "inwardly" and "outwardly" refer to directions toward and away from, respectively, the geometric center of the exemplary sterilizing apparatus and designated parts thereof. The terminology includes the words above specifically mentioned, derivatives thereof, and words of similar import. Additionally, the word "a," as used in the specification, means "at least one."

Figure 9:
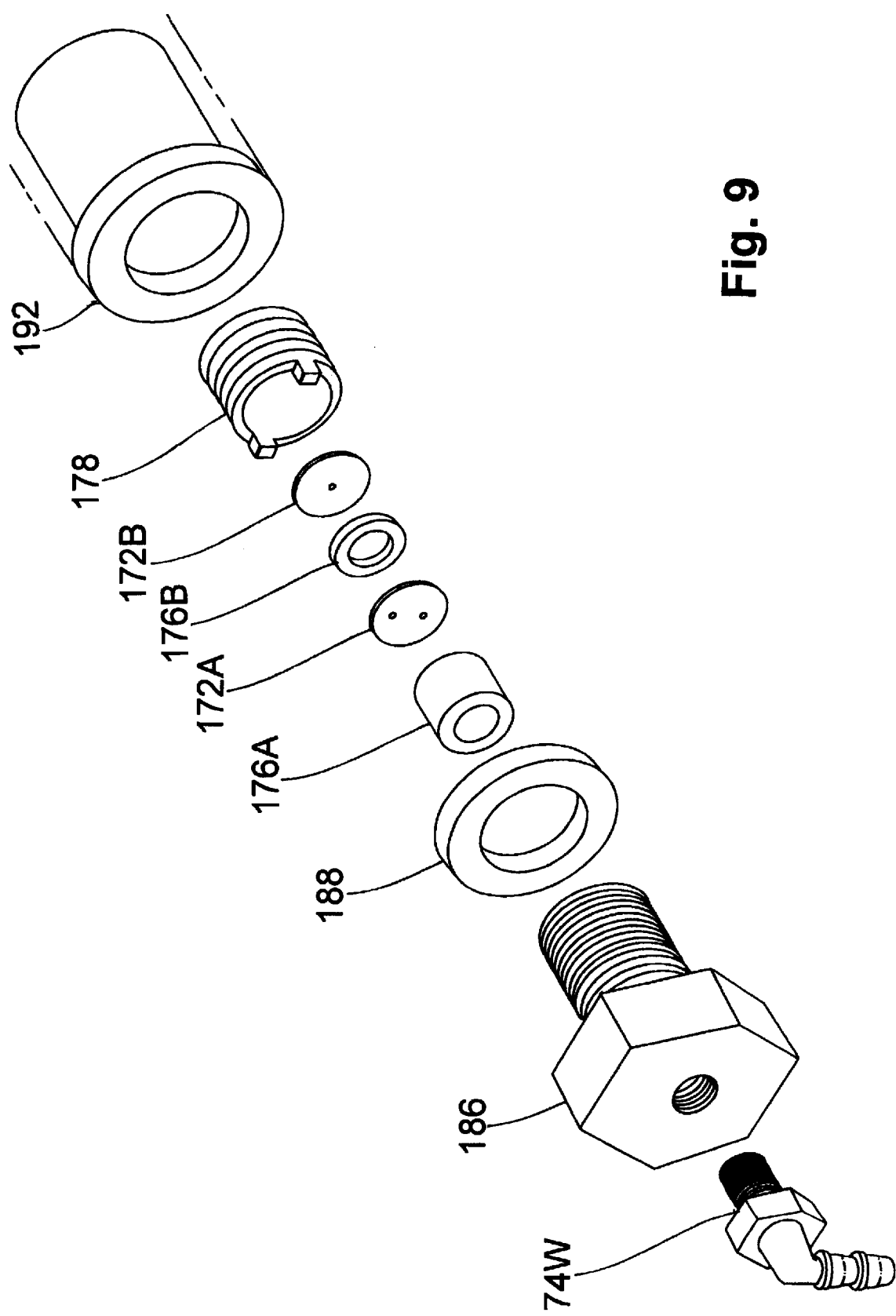
FIG. 9 is an exploded perspective view of the nozzle of FIG. 8.
Figure 10:
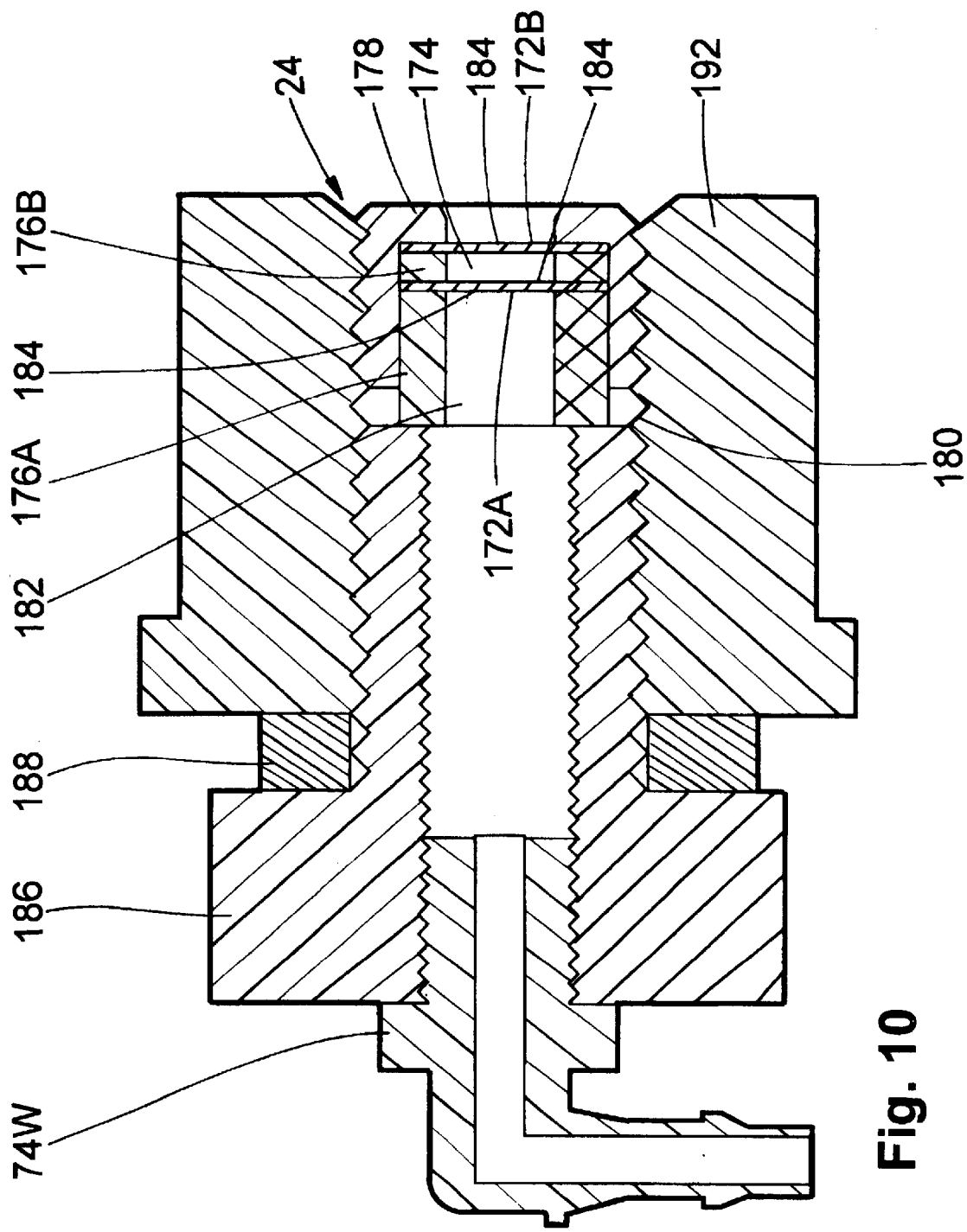
FIG. 10 is a perspective view of the exploded nozzle of FIG. 9 aligned for insertion into the chamber of FIG. 1.
Figure 11:
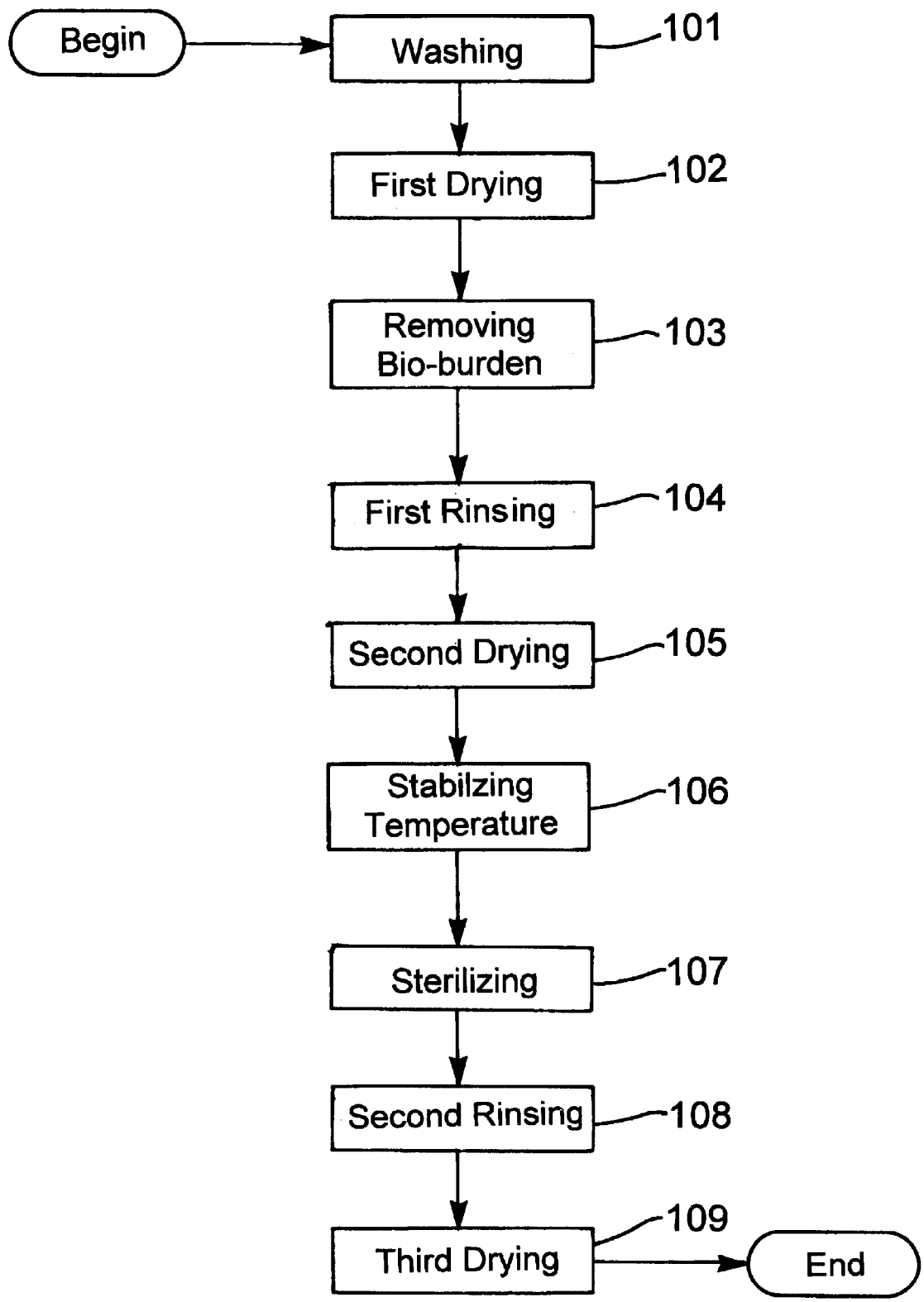
FIG. 11 is a flow diagram illustrating the steps of the preferred method of the present invention.

Referring to the drawings in detail, wherein like numerals indicate like elements throughout, there is shown in FIG. 11 a flow chart illustrating a preferred embodiment of a method of sterilizing an instrument according to the present invention. FIGS. 1–10 depict portions of an exemplary sterilizing apparatus, generally designated 10, which can be used with the preferred embodiment of the method of the present invention. The apparatus 10 is described in detail in U.S. patent application No. 09/425,261 now U.S. Pat. No. 6,379,614 which was filed on Oct. 22, 1999 and which is hereby incorporated by reference herein in its entirety. The method of the present invention can be performed using various sterilizing apparatuses. Accordingly, those of ordinary skill in the art will appreciate from this disclosure that the disclosed sterilizing apparatus 10 is but one example of a sterilizing apparatus that can be used with the method of the present invention. Briefly speaking, the method of the present invention uses the systematic application of fluids to completely sterilize an instrument mounted in a sterilizer.

The preferred instrument 12 for use with the method of the present invention is a dental handpiece. However, those of skill in the art will appreciate from this disclosure that instruments other than dental handpieces can be sterilized using the method of the present invention. For example, scalpels, forceps, prongs, endoscopes, tubes, trays, or any instrument used in a sterile lab, operating room, manufacturing site or the like can be sterilized in a quick and convenient manner using the method of the present invention. Accordingly, while the preferred instrument 12 is discussed below as having an interior 28 (as is common in dental handpieces, endoscopes, tubes, scopes and the like), those of skill in the art will appreciate from this disclosure that the method of the present invention is not limited to use with instruments 12 having an interior 28. Thus, instruments such as a scalpel or the like can be used with the method of the present invention without departing from the scope of the invention.

Referring to FIG. 1, one possible apparatus 10 for sterilizing an instrument 12 at substantially room temperature is shown. The instrument 12 has an exterior surface 32 which has a proximal end 162 that is attachable to the chamber 14. When the apparatus 10 of the present invention is used with a dental handpiece, a distal end 164 of the instrument 12 houses a rotary turbine 160. Additionally, the dental handpiece 12 has a pair of lumens 124A, 124B, which extend from the proximal end 162 of the instrument 12. The first lumen 124A transports air and the second lumen 124B transports water to the distal end of the instrument 12. Air is injected into the handpiece 12 through the first large lumen 128A to turn the rotary turbine 160. Then, the air is exhausted through the second large lumen 128B. The first and second large lumens 128A, 128B each extend from the proximal end 162 of the instrument 12 to facilitate, in combination with a threaded portion 132 of the handpiece 12, the attachment of the dental handpiece 12 to a dental apparatus (not shown). Referring to FIG. 2a, a portion of the proximal end 162 of the dental handpiece preferably has threads 132 for securing the dental handpiece to the appropriate dental apparatus (not shown).

Referring to FIGS. 1, 4, and 5, the apparatus 10 includes a chamber 14 having an interior compartment 18 for receiving and housing the instrument 12. The chamber 14 is preferably generally cylindrically shaped. However, those of skill in the art will appreciate from this disclosure that the chamber 14 may be rectangularly shaped, triangularly shaped, cubically shaped or the like.

Figures 6, 7:
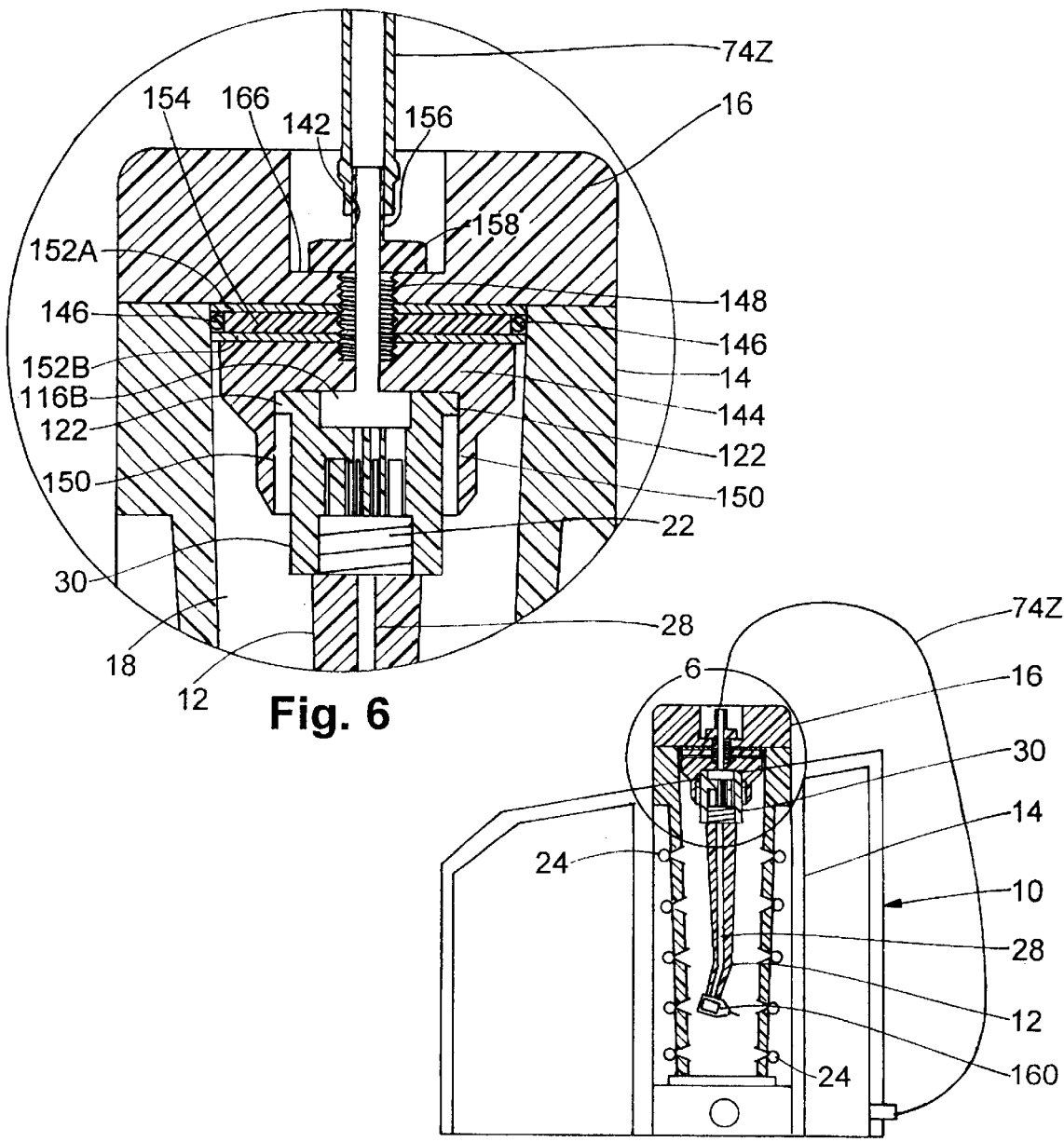
FIG. 6 is an enlarged cross-sectional view of a portion of the instrument after the instrument has been securely mounted in an interior compartment of the chamber of FIG. 1.
FIG. 7 is a cross-sectional view of the instrument mounted within the interior compartment of the chamber of FIG. 1.

The chamber 14 includes a cover or lid 16, which is removably attachable to the chamber 14. Referring to FIG. 4, during the sterilization process the instrument 12 is attached the lid 16 via a coupler 30, further described below. Referring to FIGS. 4, 5, and 6, the lid 16 includes a coupler housing 144. The coupler housing 144 is attached on an inner surface of the lid 16 and projects into the interior compartment 18 of the chamber 14 when the lid 16 is positioned to seal the chamber 14.

Referring to FIGS. 6 and 7, the coupler housing 144 is secured to the lid 16 via a fastening member 148, which extends inwardly into the chamber 14 from a sleeve member 156. The sleeve member 156 is designed to engage a twenty-sixth conduit 74Z of a fluid injection mechanism 20, further described below, and forms a channel through the lid 16 of the chamber 14 to transfer fluids into the chamber 14. The sleeve member 156 is preferably tubular shaped and capable of slidably engaging the twenty-sixth conduit 74Z. The lower end of the sleeve member 156 forms a base 158 which abuts an outer surface of the lid 16. The fastening member 148 is preferably integrally formed with the base 158 of the sleeve member 156 which is positioned in a recess 166 in the outer surface of the lid 16. The lower end of the fastening member 148 extends through the lid 16 and into the coupler housing 144. Thus, the fastening member 148 braces the lid 16 between the coupler housing 144 and the base 158 of the sleeve member 156.

The conduits used with the apparatus 10 are preferably polyethylene and/or nylon and have an external diameter of about four millimeters and an internal diameter of about two and one half millimeters. However, those of ordinary skill in the art will appreciate from this disclosure that the particular materials and size of the conduits can be changed. For example, any type of conduits can be used that can withstand the pressures, temperatures, and fluids used with the apparatus 10 without departing from the scope of the present invention. Additionally, the size of the conduits can be adjusted depending on the flow rates and pressures which are used with the apparatus 10 without departing from the scope of the present invention.

First and second plates 152A, 152B are interposed between the lid 16 and the coupler housing 144. The first plate 152A is flush against the inner surface of the lid 16, and the second plate 152B is positioned a predetermined distance from the first plate 152A via a spacer 154. Around the spacer 154, is a seal, such as an O-ring, 146 which is used to form a seal between the interior compartment 18 of chamber 14 and the surroundings. The fastening member 148 extends downwardly from the base 158 of the sleeve member 156, through the lid 16, through the first and second plates 152a, 152b, through the spacer 154, and then securely engages the coupler housing 144. Referring to FIG. 6, clips 150 are preferably attached inside the coupler housing 144 and are generally positioned on the left and right sides of the coupler 30. The clips 150 secure the coupler 30 within the coupler housing 144 to facilitate the sterilization of the instrument 12. However, those of skill in the art will appreciate from the present disclosure that various other structures or methods can be used to secure the coupler 30 to the coupler housing 144. For example, a friction-fit, interlocking prongs, a latching member or the like can be used to secure the coupler 30 to the coupler housing 144.

The chamber 14 is preferably formed of polyethylene tetrachloride. However, those of skill in the art will appreciate that the chamber 14 may be formed of any material having suitably low absorption and high acid resistance such as, inconnel, stainless steel, composites, or the like.

While the lid 16 preferably includes the first and second plates 152A, 152B, the spacer 154, the seal 156, the coupler housing 144, and the fastening member 148, those of skill in the art will appreciate from this disclosure that the particular configuration used to attach the coupler 30 to the lid 16 can vary depending on the sterilizer used with the method of the present invention. One important aspect of the lid 16 is that the lid 16 is capable of receivably engaging and supporting the instrument 12 within the chamber 14.

The interior compartment 18 is preferably maintained at a predetermined compartment temperature while the instrument 12 is being sterilized. The chamber 14 is releasably engagable with a portion 22 of the instrument 12 to support the instrument 12 within the interior compartment 18. Referring to FIGS. 2a, 6, and 7, the portion 22 of the instrument 12 bears threads 132 which are used to attach the instrument 12 to an apparatus (not shown). Referring to FIGS. 2a, 2b, and 3, the instrument 12 is attached to the coupler 30 by inserting the instrument 12 into the coupler 30. Then, referring to FIG. 4, the coupler 30 and the associated instrument 12, is inserted into the coupler housing 144 of the lid 16.

The coupler 30 is removably attached to the interior compartment 18 and is engagable with the portion 22 of the instrument 12 to secure the instrument 12 within the chamber 14. Referring to FIGS. 2b and 3, the coupler 30 preferably, but not necessarily, has a cylindrical shape. Referring to FIGS. 6 and 7, the coupler 30 supports the instrument 12 inside of the sterilizing apparatus 10. The coupler preferably includes a first body 34 having a first end 112A and a second end 112B. The first body 34 receivably engages a portion 22 of the instrument 12 on the second end 112B.

Referring to FIGS. 2c and 2d, the first body 34 has shaped notches, or recesses, 116A, 130, 126 which are designed to engage the particular instrument 12 being used with the apparatus 10. The configuration of the first body 34 can be designed to generically fit multiple instruments 12 or it can be designed to specifically connect with a particular type of instrument 12. For example, the first body 34 illustrated in FIGS. 2b, 2c, and 2d has specifically shaped recesses 116A, 126, 130 to facilitate the attachment of a dental handpiece, or any other instrument 12, to the coupler 30. The shape of the preferred first body 34 is specifically designed for use with dental handpieces. However, those of ordinary skill in the art will appreciate from this disclosure that the first body 34 can have other shapes to specifically engage other types of instruments 12. The second end 112B of the coupler 30 has a first recess 116A which includes large lumen receivers 130 that accommodate the large lumens 128A, 128B located on the proximal end 162 of the handpiece 12. Additionally, the first recess 116A also includes lumen receivers 126 for receiving the lumens 124A, 124B from the dental handpiece 12.

A second body 114 substantially surrounds the first body 34 to cause a flow of a fluid that enters the first end 112A to flow toward the second end 112B of the first body 34 The second body is preferably formed of a polyethylene material. However, those of ordinary skill in the art will appreciate from this disclosure that any non-porous material having suitable anti corrosion and low absorption properties can be used. The second body 114 preferably has a circumferential lip 168 extending around the second end 112B of the coupler 30 and projecting radially inward. Referring to FIG. 2b, the second body 114 has an inwardly projecting member 202 which forms a key for properly aligning the coupler 30 with the coupler housing 144. The projecting member 202 has a rectangular shape and extends along the entire longitudinal length of the inner surface of the second body 114.

The first body 34 directs a flow of the fluid into the interior 28 of the instrument 12. The second end 112b of the coupler 30 preferably has a first recess 116A for receivably engaging the instrument 12 in a friction fit.

The coupler 30 preferably has a second recess 116B on a first end 112A for receiving the fluid. Referring to FIGS. 2c and 2d, the coupler 30 preferably, but not necessarily, includes at least one chute, or small lumens receivers, 126 and one large intake lumen receiver 130, which extends between the first recess 116A and the second recess 116B to direct the flow of the fluid into the interior 28 of the instrument 12. The coupler 30 preferably directs a flow of the fluid into any interior 28 of the instrument 12 that has a fluid pathway connection to the portion 22 of the instrument 12 engaged by the chamber 14. Referring to FIGS. 2b and 2d, the coupler 30 includes a pair of prongs 122 extending outwardly from the second body 114. The first body 34 can be a separate piece that allows the portion 22 of the instrument 12 to be threadably engaged therein. A removable first body 34 can be located at the distal end of the coupler 30 (i.e., the end of the coupler 30 closest to the handpiece 12) for ease of attachment.

Referring to FIG. 1, the chamber 14 preferably includes a first sensor 36A for detecting when the chamber 14 is closed. The first sensor 36A is preferably a non-contact magnetic proximity sensor of the sort that is well known in the art. However, those of skill in the art will appreciate from this disclosure that any sensor capable of determining when the lid 16 is secured to the chamber 14 can be used. A second sensor 36B detects when the instrument 12 is positioned within the interior compartment 18. The second sensor 36B is preferably an infrared sensor. However, those of skill in the art will appreciate from this disclosure that any sensor capable of detecting when the instrument 12 is positioned within the interior compartment 18 without interfering with the sterilization process can be used. A third sensor 36C detects a temperature of the interior compartment 18. The third sensor is preferably a thermocouple. However, those of ordinary skill in the art will appreciate from this disclosure that any sensor capable of detecting the compartment temperature can be used.

A controller 92 is operatively engaged with the chamber 14, a fluid injection mechanism (further detailed below) 20, the first sensor 36A, the second sensor 36B, and the third sensor 36C for regulating the flow of the fluid through the apparatus 10. The controller 92 preferably uses an ATMEL 89C52 processor. However, those of ordinary skill in the art will appreciate from this disclosure that any suitable imbedded microprocessor assembly can be used to control and monitor the apparatus 10. The processor is preferably attached to a customized control board having customized hardware interface electronics that are adapted for use with the sterilizing apparatus 10.

A specially designed software program activates all the processes and monitors, in real time, the accuracy of the steps used to sterilize the instrument 12. Referring to FIGS. 4 and 5, a liquid crystal display 170 is preferably used to monitor the functions of the apparatus 10 while a printer 136 preferably prints out an operational log 134 detailing the various operations of the apparatus 10.

Referring to FIG. 10, the chamber 14 preferably has multiple nozzle receivers 194. Each nozzle receiver 194 preferably includes a tubular projection 206 which extends outwardly from the outer surface of the chamber 14. The tubular projections 206 enclose a chute 204 that extends through the tubular projection 206 and through the wall of the chamber 14. The chute 204 allows a nozzle (further detailed below) 24 to be secured therein. Two sensor receivers 196 are shown on the chamber 14. The sensor receiver 196 closer to the top of the chamber is preferably designed for use with the second sensor 36B which is used to determine whether an instrument 12 is positioned within the chamber 14. The sensor receiver 196 that is positioned closer to the bottom of the chamber 14 is preferably designed for use with the third sensor 36C which detects the temperature of the interior compartment 18.

While a preferred embodiment of the chamber has been described in detail above, those of skill in the art will appreciate from this disclosure that various structural features of the chamber 14 can be altered. For example, the particular connections between the instrument 12 and the chamber 14 may be varied as long as proper sterilization of the instrument 12 is not affected.

The fluid injection mechanism 20 is in fluid communication with the chamber 14 for supplying fluid to the chamber 14 and for maintaining the fluid at a predetermined fluid temperature while the instrument 12 is being sterilized. The fluid injection mechanism 20 uses a combination of fluid pumps (further detailed below) 72A–72C and pressurized air to transport appropriate fluids, further detailed below, through the chamber 14 for the cleaning and sterilizing of the instrument 12. The fluid is delivered by the fluid injection mechanism 20 to the chamber using either the twenty-sixth conduit 74Z or using a twenty-third conduit 74W.

The predetermined compartment temperature and the predetermined fluid temperature are preferably maintained within the range of between about fifty-five degrees Fahrenheit and about ninety-five degrees Fahrenheit during the sterilization of the instrument 12. This allows the instrument 12 to be sterilized while only being exposed to substantially room temperatures and thus prevents damage to thermosensitive instruments 12, such as dental handpieces. The currently preferred predetermined compartment temperature and the currently preferred predetermined fluid temperature are within the range of between about ninety degrees Fahrenheit and about ninety-four degrees Fahrenheit during the sterilization of the instrument 12. While preferred ranges have been detailed above, those of skill in the art will appreciate from this disclosure that the preferred temperature ranges assume an exposure of the instrument 12 to a sterilizing fluid 50 comprising a peracetic acid, further detailed below, for a time period between about three minutes and about six minutes. Additionally, the above temperature ranges are preferred for an apparatus 10 that completes the sterilization process, further detailed below, within a time period between of about ten minutes and about twelve minutes. Those of skill in the art will appreciate from this disclosure that if the time periods for completion of the sterilization process, or the associated exposure of the instrument to the sterilizing liquid were increased, or if a different type of sterilizing fluid were used with the apparatus then temperatures other than those detailed above could be used in combination with the apparatus 10.

The fluid used by the apparatus 10 is any one of a rinse fluid 46, a bio-burden removal fluid 48, a sterilizing fluid 50, and filtered air. The rinse fluid 46 preferably comprises sterilized water. However, those of skill in the art will appreciate from this disclosure that any suitably sterile fluid capable of rinsing the instrument 12, which is safe for exposure to and consumption by patients can be used as the rinse fluid 46. The bio-burden removal fluid 48 preferably comprises a protease fluid. However, those of skill in the art will appreciate from this disclosure that any fluid capable of safely removing bio-burden from a soiled instrument 12 to simplify the killing of pathogen can be used as the bio-burden removal fluid 48. The sterilizing fluid 50 preferably comprises a peracetic acid. However, those of skill in the art will appreciate that the sterilizing fluid 50 may contain any components, which contribute to the killing of pathogens and are safe for use at a patient-side location.

The chamber 14 includes at least one fluid outlet 24 for directing a flow of the fluid onto the exterior surface 32 of the instrument 12. Referring to FIGS. 1 and 7, twelve spaced fluid outlets 24 are preferably used in the chamber 14. However, those of skill in the art will appreciate from this disclosure that any number of fluid outlets 24 may be used to direct fluid onto the exterior surface 32 of the instrument 12 as long as proper amounts of the fluid can be directed onto the exterior surface 32 of the instrument 12. When the fluid injection mechanism sends fluid to the fluid outlets 24, fluid is transported along the twenty-second conduit 74V to a twenty-third conduit 74W which guides the fluid into each of the fluid outlets 24.

Figure 8:
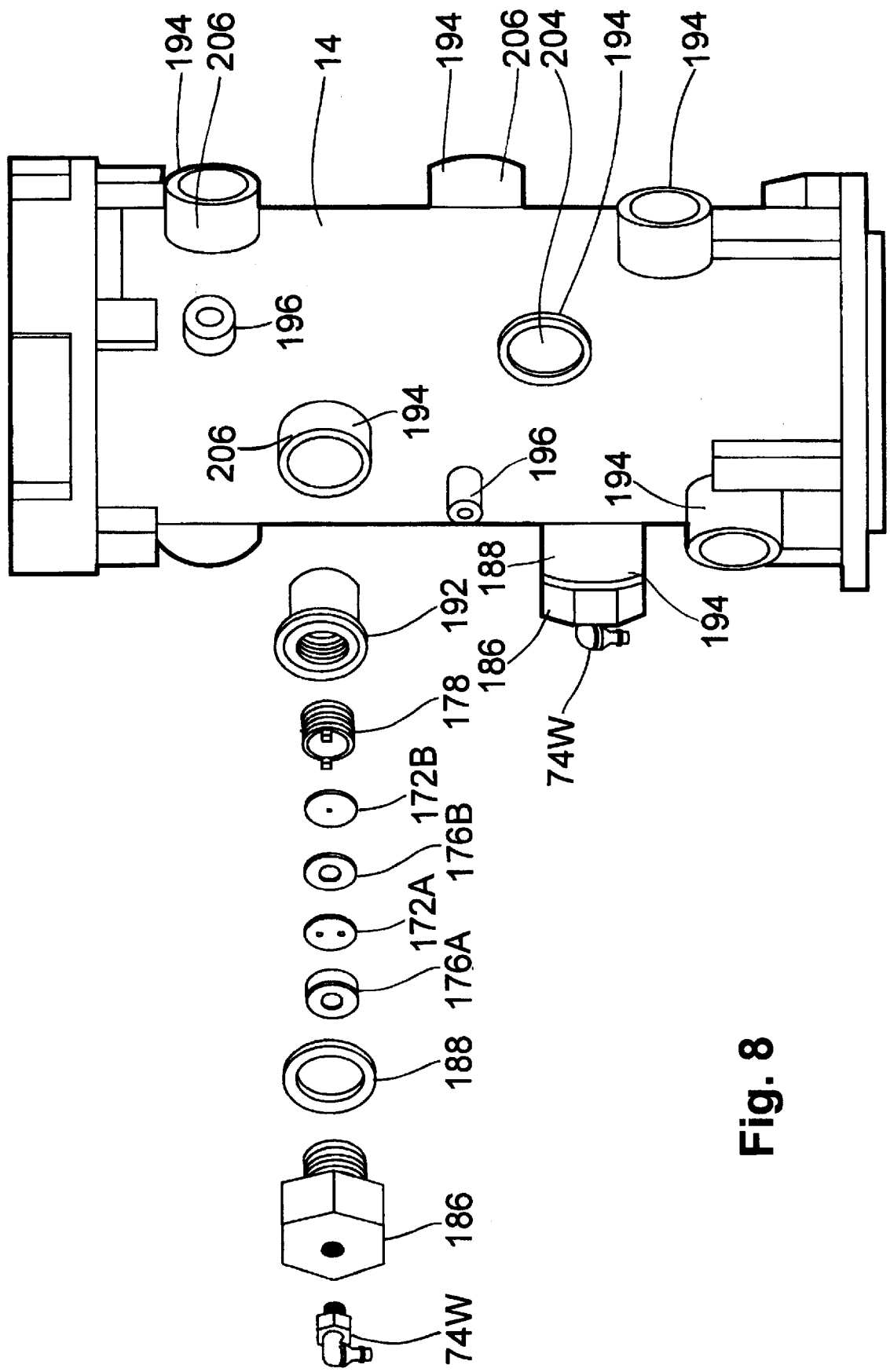
FIG. 8 is a cross-sectional view of a nozzle, which is not mounted into the chamber of FIG. 1.

The at least one fluid outlet 24 preferably, but not necessarily, comprises at least one nozzle 24 mounted to the chamber 14 to direct the flow of the fluid onto the exterior surface 32 of the instrument 12. Referring to FIGS. 8–10, each nozzle 24 is preferably inserted in the inner surface of the chamber 14. The spraying action of the nozzle is preferably caused by first and second nozzle plates 172A, 172B. The nozzle plates 172A, 172B are preferably disposed in a spaced apart parallel planar fashion to create a compartment 174 therebetween where turbulent fluid flow takes place as further detailed below. The nozzle 24 preferably includes a first and second generally annular spacer 176A, 176B, which are used to hold the first and second nozzle plates 172A, 172B in a spaced apart generally parallel planar fashion.

The first and second spacers 176A, 176B are preferably formed of a low absorption and non-reactive material such as nylon or the like. The first spacer 176A receives a fluid from the fluid injection mechanism 20, further detailed below. The first nozzle plate 172A has a first and second surface. The first surface is disposed on a distal end of the first spacer 176A and has at least one, but preferably two holes 184 extending therethrough. The second spacer 176B is disposed on the second surface of the first nozzle plate 172A and the second nozzle plate 172B is attached on an opposite end of the second spacer 176B from the first nozzle plate 172A and has a hole 184 therein. The first and second nozzle plates 172A, 172B and the first and second spacers 176A, 176B are held in position by a nozzle retainer 178. The nozzle retainer 178 is preferably circularly shaped to facilitate the threaded engagement between the nozzle retainer 178 and the threaded bore 180 which is disposed in a nozzle insert 192. It is preferable that the first and second nylon spacers 176A, 176B and the first and second nozzle plates 172A, 172B are circularly shaped. However, those of skill in the art will appreciate from this disclosure that the first and second nylon spacers 176A, 176B and the first and second nozzle plates 172A, 172B may have other shapes when viewed along the longitudinal axis of the nozzle 24.

Referring to FIGS. 8–10, the first nozzle plate 172A is positioned on the right side of the first nylon spacer 176A to form a chamber 182. The second nylon spacer 176B is positioned on the opposite side of the first nozzle plate 172A from the first nylon spacer 176A. The second nozzle plate 172B is positioned on the right side of the second nylon spacer 176B to form the compartment 174.

The first nozzle plate 172A has two holes 184 which allow fluid to pass from the chamber 182 into the compartment 174. A single hole 184 is preferably positioned in the second nozzle plate 172B. The combination of the positioning of the two holes 184 in the first nozzle plate 172A and the positioning of the one hole 184 in the second nozzle plate 172B combine to generate a turbulent fluid flow within the compartment 174 which results in the emission of a vigorous spray of the fluid from the hole 184 in the second nozzle plate 172B. The turbulent fluid flow in compartment 174 results in the spray having a shape similar to a cone with an angular width of about ninety degrees as measured from the hole 184 in the second nozzle plate 172B.

The first and second nozzle plates 172A, 172B and the nozzle retainer 178 are preferably formed of inconnel but may be formed of any low absorption corrosion resistant material capable of withstanding the fluid pressures used by the apparatus 10 such as other types of stainless steel or composites or the like. Engaged with the side of the nozzle 24 opposite from the interior compartment 18 of the chamber 14 is a conduit-securing bolt 186. The conduit securing bolt 186 is threadably inserted into the bore 180 in the nozzle insert 192 to form a fluid passageway between the twenty-third conduit 74W of the fluid injection mechanism 20 and the chamber 182 of the nozzle 24. A seal, such as an O-ring, 188 is preferably positioned between the flange of the conduit securing bolt 186 and the exterior surface of the nozzle insert 192.

Referring to FIG. 1, the fluid injection mechanism 20 includes reservoirs 44A, 44B, or 44C for storing the fluid and conduits extending between the reservoirs 44A–44C and the chamber 14. Pumps 72A, 72B, or 72C remove fluid from the reservoirs 44A, 44B, or 44C and drive the fluid through the conduits toward the chamber 14. The first and second pumps 72A, 72B which are used with the rinse fluid 46 and the bio-burden removing fluid 48 are preferably liquid diaphragm pumps. The third pump 72C which is used with the sterilizing fluid 50 is preferably a modified liquid diaphragm pump. More specifically, the third pump 72C is preferably a liquid diaphragm pump that has been modified to also act as a metering pump. The modified third pump 72C permits improved control over the amount of sterilizing fluid 50 which is used by the apparatus 10.

Additionally, the fluid injection mechanism 20 includes air valves 76A, 76B, 76C, or 76D for supplying pressurized air to remove fluid from the conduits and propel the fluid toward the chamber 14. The fluid injection mechanism 20 further includes heaters 88A–88D, 90 to maintain the fluid at approximately the predetermined fluid temperature.

The first through fourth heaters are preferably part of an independent thermal control circuit. Each heater preferably, but not necessarily, comprises a heating element, such as copper or the like, which is wrapped around the heater chamber and sealed with a jacket that covers the heating element. A thermocouple is preferably combined with the heaters 88A–88B to allow for the detection of the temperature of the fluid contained therein. Each thermal control circuit monitors the temperature of the associated fluid and automatically powers the heater 88A,–88D as necessary to bring the fluid substantially to the predetermined fluid temperature. Accordingly, each thermal control circuit preferably controls a respective heater so that all the controller 92 needs to monitor is the temperature of the fluid. Assuming the temperature of the fluid is within the predetermined range, the controller 92 will operate the rest of the liquid injection mechanism as further detailed below.

More specifically, the rinse fluid 46 is preferably contained within a first reservoir 44A, the bio-burden removal fluid 48 is preferably contained within a second reservoir 44B, and the sterilizing fluid 50 is preferably contained within a third reservoir 44C. Each of the reservoirs 44A–44C has an associated pump 72A–72C, which initially transports the fluid toward the chamber 14.

A heater is preferably not used to heat the bio-burden removing fluid 48 because the bio-burden removing fluid 48 is substantially brought to the predetermined fluid temperature due to the heat generated by the rinse fluid 46, the sterilizing fluid 50, the pressurized air, and the heater 90 which maintains the chamber 14 at the predetermined compartment temperature. Due to the relatively higher mass of the instrument 12 and the chamber 14, the bio-burden removing fluid 48 is heated to the predetermined fluid temperature without significantly altering the temperature of the instrument 12 or the chamber 14. Those of skill in the art will appreciate from this disclosure that a heater for the bio-burden removing fluid can be incorporated with the apparatus 10.

Pressurized atmospheric air preferably enters the apparatus 10 via an inlet 94, which is attached to an air filter 96. The pressurized air is preferably supplied by a compressor (not shown) which is external to the apparatus 10. However, those of ordinary skill in the art will appreciate from this disclosure that a compressor could be incorporated with the apparatus 10. The apparatus preferably uses about one cubic foot of air per minute at about seventy-five pounds per square inch. However, those of ordinary skill in the art will appreciate from this disclosure that the amount of pressurized air that is used by the apparatus 10 can be modified depending on the size of the apparatus 10 and depending on the flow rates that the apparatus is designed to use.

The air filter 96 filters and guides the pressurized air to a pressure regulator 100, which is monitored via a pressure gauge 98. The pressure of the pressurized air is preferably in the range of between about 75 pounds per square inch and about 85 pounds per square inch. However, those of skill in the art will appreciate from this disclosure that the pressure of the pressurized air can be varied depending upon the specific components used to form the apparatus 10.

In the event of excessive pressure in the air filter 96, automatic discharge valves 102 open and cause air to be dumped from the apparatus via a seventh conduit 74G, through a fourteenth checkvalve 86N, and out through the apparatus outlet 66. Once the filtered air is transported past the pressure regulator 100, the pressurized air is heated using a first heater 88A and is then transported along a first conduit 74A. The pressure of the filtered air in the first conduit 74A is monitored by an inlet air pressure sensor 104. The inlet air pressure sensor 104 is preferably an electronic transducer. However, those of skill in the art will appreciate that any sensor capable of reliably monitoring the inlet air pressure can be used. The first conduit 74A supplies air to first through fourth air valves 76A–76D and a drain air valve 64 via second through sixth conduits 74B–74F respectively.

The checkvalves of the present invention are preferably acid resistant and relatively small sized. For example, the checkvalves of the present invention are preferably one half inch in length and one half inch in diameter. The checkvalves are preferably designed to interface with conduits that have an external diameter of about four millimeters.

Each of the first through fourth air valves 76A–76D and the drain air valve 64 are connected via an eighth conduit 74H to an air exhaust valve 188. Each of the air valves 76A–76D is shown in the first, or disengaged, position 40. While the first through fourth air valves 76A–76D, and the drain air valve 64 are in the first position 40, the exhaust valve 188 prevents pressurized air from remaining in the conduits connecting the respective air valves to the portion of the fluid injection mechanism 20 which transports the fluids, further detailed below. The first through fourth air valves 76A-76D and the drain air valve 64 are preferably SMC™ air valves. The air valves are compact and measure about a half-inch in length and have a half inch diameter. Each air valve preferably has a power consumption of about one half a Watt.

Referring to the first air valve 76A, the first air valve 76A is biased into the first position 40 via a first input biasing element 78A. When the first air valve 76A is in the first position 40, any pressurized air in a ninth conduit 74I is diverted through the eighth conduit 74H to the exhaust valve 188. A switch 80A is capable of moving the first air valve 76A from the first position 40 into the second position 42 which causes the filtered pressurized air that is supplied via the second conduit 74B to be applied to the ninth conduit 74I and through a first checkvalve 86A.

Referring to the second air valve 76B, the second air valve 76B is biased into the first position 40 by a second input biasing element 78B. While the second air valve 76B is in the first position 40, any pressurized air in a tenth conduit 74J is diverted to the exhaust valve 188 via the eighth conduit 74H. A second switch 80B can move the second air valve 76B into the second position 42 which causes filtered, pressurized air in the third conduit 74C to be applied to the tenth conduit 74J and driven through a third checkvalve 86C into the eighteenth conduit 74R.

Referring to the third air valve 76C, the third air valve 76C is biased into the first position 40 by a third input biasing element 78C. While the third air valve 76C is in the first position 40, any pressurized air in an eleventh conduit 74K is diverted to the exhaust valve 188 via the eighth conduit 74H. A third switch 80C can move the third air valve 76C into the second position 42. When the third air valve 76C is in the second position 42, filtered pressurized air from the fourth conduit 74D is provided to the eleventh conduit 74K. When pressurized air is driven into the eleventh conduit 74K, the air is guided to an air diverter valve 108.

The air diverter valve 108 has a second diverter switch 110B capable of moving the air diverter valve 108 between a first position 40 and a second position 42. The air diverter valve 108 is shown in the second position 42 in FIG. 1. While the air diverter valve 108 is in the second position 42, air from the eleventh conduit 74K is provided to a nineteenth conduit 74S and driven through a ninth checkvalve 86I. When the air diverter valve 108 is in the first position 40, pressurized air from the eleventh conduit 74K is provided to a twentieth conduit 74T and driven through a sixth checkvalve 86F. The operation and positioning of the air diverter valve 108 is further discussed below.

Referring to the fourth air valve 76D, a fourth input biasing element 78D biases the fourth air valve 76D into the first position 40. While the fourth air valve 76D is in the first position 40, any pressurized air in twelfth conduit 74L is diverted to the exhaust valve 188 via the eighth conduit 74H. A fourth switch 80D is capable of moving the fourth air valve 76D into the second position 42. While the fourth air valve 76D is in the second position 42, filtered pressurized air from the fifth conduit 74E is provided to the twelfth conduit 74L and driven through an eleventh checkvalve 86K.

Referring to the drain air valve 64, the drain air valve 64 is biased into a first position 40 by a drain-biasing element 82. While the drain air valve 64 is in the first position 40, pressurized air in a thirteenth conduit 74M is diverted to the exhaust valve 188 via the eighth conduit 74H. A drain switch 84 is capable of moving the drain air valve 64 into the second position 42. While the drain air valve 64 is in the second position 42, pressurized air from a sixth conduit 74F is provided to the thirteenth conduit 74M and driven through a restrictor 190 and a thirteenth checkvalve 86M. The restrictor 190 reduces the flow of the filtered pressurized air through the thirteenth checkvalve 86M. The restrictor 190 is preferably used because the flow of the pressurized air from the drain air valve 64 is in excess of that which is desired to create a suction effect to remove fluid from the chamber, as further detailed below.

Each of the first through fourth switches 80A–80D and the drain switch 84 are preferably integral with the SMC™, or similar type, air valve and are air assisted switches. In other words the switches are moved partially using electric power and then, are moved the rest of the way using a portion of the pressurized air. However, those of ordinary skill in the art will appreciate from this disclosure that the first through fourth switches 80A–80D may be separate components from their respective air valves. For example, electrically operated solenoid switches that are controlled by the controller 92. However, those of ordinary skill in the art will appreciate from this disclosure that any type of switch used for the positioning of valves can be used.

Rinse fluid 46 is removed from the first reservoir 44A and driven through a fourteenth conduit 74N by the first pump 72A. During one complete sterilization operation of the apparatus 10 about fifty millimeters to about one hundred fifty milliliters of rinse fluid 46 is preferably used. However, those of ordinary skill in the art will appreciate from this disclosure that depending on the size of the apparatus 10 and depending upon the type of rinse fluid 46 used, the amount of rinse fluid 46 that is processed by the apparatus 10 during one complete sterilization operation can be varied. An exhaust valve 200 is attached to the first reservoir 44A to allow air to enter the first reservoir 44A and to reduce the amount of force that must be generated by the first pump 44A to remove the rinse fluid 46 from the first reservoir 44A. The rinse fluid 46 is then driven through a second checkvalve 86B to the second heater 88B. The second heater 88B ensures that the rinse fluid 46 is at the predetermined fluid temperature prior to the controller 92 applying the rinse fluid 46 to the instrument 12 contained within the chamber 14, further detailed below. To apply the rinse fluid 46 to the instrument 12 contained within the chamber 14, the first pump 72A in combination with the first, second, and fourth air valves 76A, 76B, and 76D drives the rinse fluid 46 into the chamber 14 as described below.

To transfer the rinse fluid 46 from the second heater 88B to the chamber 14, the first air valve 76A is moved into the second position 42 to provide pressurized air to the ninth conduit 74I. When pressurized air is transferred through the ninth conduit 74I, the pressurized air passes the first checkvalve 86A to push heated fluid from the second heater 88B into a seventeenth conduit 74Q which guides the rinse fluid 46 to the first fluid sensor 106A. Then, the rinse fluid 46 is driven the past the fourth checkvalve 86D and into the eighteenth conduit 74R.

The second air valve 76B is then moved into the second position 42 to transfer pressurized air into the tenth conduit 74J, past the third checkvalve 86C, and into the eighteenth conduit 74R to push the rinse fluid 46 toward a diverter valve 38. The diverter valve 38 guides the rinse fluid 46 (or either one of the bio-burden removing fluid 48 and the sterilizing fluid 50, as appropriate) toward either the portion 22 of the instrument 12 that is engaged by the chamber 14 or toward the fluid outlets 24 disposed in the walls of the chamber 14. When the diverter valve 38 is in the first position 40; the rinse fluid is transferred to the twenty-second conduit 74V and into the twenty-third conduit 74W. Then, the fourth air valve 76D is moved into the second position 42 to transfer pressurized air from the fifth conduit 74E to the twelfth conduit 74L and then through the eleventh checkvalve 86K. The pressurized air that is driven through the eleventh check valve 86K aids in driving the rinse fluid 46 contained in the twenty-third conduit 74W into the fluid outlets 24 for application onto the exterior 32 of the instrument 12 contained within the chamber 14.

Alternatively, when the diverter valve 38 is in the second position 42, the rinse fluid 46 is transferred to the twenty-sixth conduit 74Z which guides the rinse fluid 46 to the portion 22 of the instrument 12 that is engaged with the lid 16 of the chamber 14. A first diverter switch 110A enables the diverter valve 38 to send fluid to either the fluid outlets 24 or to the portion 22 of the instrument 12 that is engaged with the chamber 14. Thus, the rinse fluid 46 is transferred to the chamber 14 due to forces provided by the first pump 72A, the first air valve 76A, the second air valve 76B, and the fourth air valve 76D.

The first and second diverter switches 110A, 110B are preferably integral with their respective air valves and can be controlled by the controller 92. However, those of ordinary skill in the art will appreciate from this disclosure that the first and second diverter switches can be electrically operated solenoid switches, electric motors or the like.

To transfer the bio-burden removing fluid 48 from a second reservoir 44B to the chamber 14, a second pump 72B drives the bio-burden removing fluid 48 through a fifteenth conduit 74O past a second fluid sensor 106B and past a fifth checkvalve 86E. Then, the bio-burden removing fluid 48 enters the eighteenth conduit 74R and is guided toward the diverter valve 38. Then, second air valve 76B is moved into the second position to guide pressurized air from the third conduit 74C to the tenth conduit 74J to aid in driving the bio-burden removing fluid 48 through the eighteenth conduit 74R to the diverter valve 38. The apparatus 10 preferably uses between about six milliliters and about twelve milliliters of bio-burden removing fluid 48 during the complete sterilization process for one instrument 12. However, those of ordinary skill in the art will appreciate from this disclosure that depending on the size of the apparatus and the type of bio-burden removing fluid 48 used, that the amount of bio-burden removing fluid used can be varied without departing from the scope of the present invention.

Depending upon the position of the diverter valve 38, the bio-burden removing fluid 48 is directed toward either the portion 22 of the instrument 12 that is engaged by the chamber 14 or toward the nozzles 24 contained in the chamber 14. When the diverter valve 38 is in the first position 40, the bio-burden removing fluid 48 enters into the twenty-second conduit 74V and is guided to the twenty-third conduit 74W.

Then, the fourth air valve 76D is moved into the second position 42 causing pressurized air to move from the fifth conduit 74E to the twelfth conduit 74L to aid in driving the bio-burden removing fluid 48 from the twenty-third conduit 74W to the fluid outlets 24 in the chamber 14 for application of the bio-burden removing fluid 48 to the exterior 32 of the instrument 12.

When the diverter valve 38 is in the second position 42, the bio-burden removing fluid 48 is transferred to the twenty-sixth conduit 74Z which guides the bio-burden removing fluid 48 to the portion 22 of the instrument 12 which is engaged by the chamber 14. Thus, the bio-burden removing fluid 48 is transferred from the second reservoir 44B to the chamber 14 by the action of the second pump 72B, the second air valve 76B, and the fourth air valve 76D.

The sterilizing fluid 50 is transferred from the third reservoir 44C to the chamber 14 as follows. The third pump 72C transfers the sterilizing fluid 50 from the third reservoir 44C to a sixteenth conduit 74P and drives the sterilizing fluid 50 through a seventh checkvalve 86G. An exhaust valve 198 is attached to the third reservoir 44C to allow air to enter the third reservoir 44C and to reduce the amount of force that must be generated by the third pump 44C to remove the sterilizing fluid 50 from the third reservoir 44C. Then, the sterilizing fluid 50 is pumped into a third heater 86C, through an eighth checkvalve 86H, and into a fourth heater 88D. Once the Sterilizing solution has filled both the third and fourth heaters 88C, 88D, a third fluid sensor 106C indicates that a complete charge of the sterilizing fluid 50 is ready for application after being heated to the predetermined fluid temperature. The sterilizing fluid 50 is preferably applied two times during the sterilization of the instrument 12 (each time providing a full charge of sterilizing fluid 50 to the instrument). The second sterilizing fluid 50 treatment is preferably applied without an intervening rinse fluid 46 application to prevent as much dilution as possible. It is preferred that the total amount of sterilant used by the apparatus 10 during the sterilization of the instrument 12 be between about six milliliters and about thirty milliliters. However, those of ordinary skill in the art will appreciate from this disclosure that greater or lessor amounts of sterilant can be used without departing from the scope of the present invention.

Then, once the sterilizing fluid 50 that is in the twenty-first conduit 74U (i.e.: in the third and fourth heaters 88C, 88D) has reached the predetermined fluid temperature, the third air valve 76C is moved into the second position 42 causing pressurized air to enter the eleventh conduit 74K. The pressurized air is guided to the air diverter valve 108, which is switched into the second position 42 to guide air into the nineteenth conduit 74S, and through the ninth checkvalve 86I. This causes the pressurized air to drive the sterilizing fluid 50 which is contained above the eighth checkvalve 86H through a tenth checkvalve 86J and into the diverter valve 38. Depending upon the position of the diverter valve 38, the sterilizing fluid 50 is either guided toward the fluid outlets 24 in the chamber 14 or toward the portion 22 of the instrument 12 which is engaged by the chamber 14.

When the diverter valve 38 is in the first position 40, the sterilizing fluid 50 is transferred to the twenty-second conduit 74V and into the twenty-third conduit 74W. Then, the fourth air valve 76D is moved into the second position 42 causing pressurized air to enter the twelfth conduit 74L. This causes pressurized air to pass through the eleventh checkvalve 86K and to drive the sterilizing fluid 50 through the twenty-third conduit 74W into the fluid outlets 24 for application to the exterior 32 of the instrument 12 contained within the chamber 14. Alternatively, when the diverter valve 38 is in the second position 42, the sterilizing fluid 50 is transferred to the twenty-sixth conduit 74Z which guides the sterilizing fluid 50 to the portion 22 of the instrument 12 which is engaged by the lid 16 of the chamber 14.

After the application of the sterilizing fluid 50 which was temporarily positioned above the eighth checkvalve 86H is completed, the air diverter valve 108 is moved into the first position 40 causing pressurized air to enter the twentieth conduit 74T and to pass through the sixth checkvalve 86F. This results in the pressurized air driving the remaining sterilizing fluid 50 that is present on the right side of the seventh checkvalve 86G toward the diverter valve 38. Once the remaining sterilizing fluid 50 reaches the diverter valve 38, the sterilizing fluid 50 is guided toward either the fluid outlets 24 in the chamber 14 or toward the portion 22 of the instrument 12 which is engaged with the lid 16 of the chamber 14, as described above.

The chamber 14 further includes at least another fluid outlet 26 to direct the flow of the fluid onto the portion 22 of the instrument 12 engaged by the chamber 14. Accordingly, as described above, fluid is guided through the twenty-sixth conduit 74Z, the fluid is directed towards the portion 22 of the instrument 12 by the other fluid outlet 26. When the instrument 12 has an interior 28 that has a fluid pathway connection to the portion 22 of the instrument 12 engaged by the chamber 14, the other fluid outlet 26 also directs a flow of the fluid into an interior 28 of the instrument 12. As the apparatus 10 of the present invention is preferably used with dental handpieces, the interior 28 of the instrument 12 is sterilized by the application of the sterilizing fluid 50 to the inside of the lumens 124A, 124B. However, those of skill in the art will appreciate from the present invention that the sterilizing apparatus 10 may be used with an instrument 12 not having an interior 28 without departing from the scope of the present invention.

The fluid injection mechanism 20 alternatingly supplies a flow of the fluid to either the one fluid outlet 24 or into the other fluid outlet 26. As detailed above, the fluid injection mechanism 20 includes a diverter valve 38 for alternately supplying a flow of the fluid to the one fluid outlet 24 and to the other fluid outlet 26. While the preferred embodiment of the present invention preferably alternately directs a flow of fluid to either the portion 22 of the instrument 12 engaged by the chamber 14 or to the nozzles 24 of the chamber 14, those of skill in the art will appreciate from this disclosure that the fluid can be supplied simultaneously to both the nozzles 24 and to the portion 22 of the instrument 12 that is engaged by the chamber 14 without departing from the scope of the present invention. For example, the diverter valve 38 can be replaced by a flow divider (not shown) or the like, to simultaneously apply the fluid to both the exterior 32 of the instrument 12 and to the portion 22 of the instrument 12 that is engaged by the chamber 14.

Referring to FIG. 1, the apparatus 10 further includes a drain 52 for removing fluid from the chamber 14, and a drain valve 54 for opening and closing the drain 52. The drain valve 54 is biased into a closed position 56 by a drain valve-biasing element 60. When the drain valve 54 is in the closed position, the fluid is prevented from exiting the chamber 14 by a twelfth checkvalve 86L. A drain switch 68 is capable of moving the drain valve 54 into an open position 58 which allows the fluid to drain from the chamber 14 into a twenty-fourth conduit 74X, which forms a waste line 70.

To facilitate draining fluid from the chamber 14, the drain air valve 64 creates a vacuum to pull the fluid out of the twenty-fourth conduit 74X. More specifically, the drain air valve 64 is shown in FIG. 1 in the first position 40. The drain air valve 64 is biased into the first position 40 by a drain air valve-biasing element 82. While the drain air valve 64 is in the first position 40, pressurized air in the thirteenth conduit 74M is transported to the exhaust valve 188 via the eighth conduit 74H.

A drain switch 84 is capable of moving the drain air valve 64 into the second position 42 which allows the drain air valve 64 to supply pressurized air to drive the fluid along the waste line 70 and through a drain nozzle 62, which is attached along the waste line 70. When the drain air valve 64 is in the second position, pressurized air from the sixth conduit 74F is provided to the thirteenth conduit 74M, through the restrictor 190, through the thirteenth checkvalve 86M, and into the waste line nozzle 62.

The airflow through the thirteenth conduit 74M creates a suction effect that pulls the fluid from the twenty-fourth conduit 74X and drives the fluid into a twenty-fifth conduit 74Y. Then, by opening the automatic discharge valves 102 a predetermined amount, air is propelled through the seventh conduit 74G and past the fourteenth checkvalve 86N. The flow of air through the seventh conduit 74G creates a further suction effect to pull the fluid from the twenty-fifth conduit 74Y to a waste line outlet 66 through which the fluid is expelled from the apparatus 10.

A method of sterilizing the instrument 12, which has an exterior surface 32 preferably includes attaching the instrument 12 to the coupler 30 prior to attaching the instrument 12 to the chamber 14 via the coupler 30. The first body 34 of the coupler 30 is preferably formed of polyethylene material. Those of ordinary skill in the art will appreciate from this disclosure that various methods can be used to attach the instrument 12 to the chamber 14 while performing the method of the present invention. The method of the present invention preferably, but not necessarily, also includes the steps of determining via a first sensor 36A whether the chamber 14 is closed and determining via a second sensor 36B whether an instrument 12 is enclosed in the chamber 14.

The instrument 12 is preferably secured inside of the chamber 14 by removably engaging a proximal end 162 of the instrument 12 with the lid 16 of the chamber 14. After an instrument 12 is placed within the chamber 14, the instrument 12 is ready for sterilizing.

The rapid sterilization of instruments 12 achieved by the method of the present invention allows for instruments 12 to be effectively sterilized during a medical procedure which requires the repetitive use of a sterile instrument 12. Those of ordinary skill in the art will appreciate from this disclosure that the amount of time to complete the method can vary depending on the chemicals used, the level of sterilization or decontamination desired, and the specific steps used in the sterilizing process. For example, the method can be adjusted to require an hour to sterilize an instrument 12 or to require less than six hundred twenty (620) seconds to complete the sterilization process.

As detailed above, in the preferred embodiment of the method of the present invention, the position of the diverter valve 38 determines whether fluid is guided onto the proximal end 162 of the instrument 12 or to the at least one fluid outlet 24 in the chamber 14. When fluid is directed onto the proximal end 162 of the instrument 12, the end of the instrument 12 that is engaged with the lid 16 of the chamber 14 is treated with the fluid. Additionally, any interior passages of the instrument 12 which have an opening on the proximal end 162 receive fluid that contacts the interior 28 of the instrument 12 when fluid is directed toward the proximal end 162 of the instrument 12. When fluid is supplied to the chamber 14, the fluid is preferably sprayed via the at least one fluid outlet 24 onto the exterior 32 of the instrument 12.

The operation of the exemplar apparatus 10 during the transfer of any one of the rinse fluid 46, the bio-burden removing fluid 48 and the sterilizing fluid 50 to either one of the proximal end 162 of the instrument 12 and the at least one fluid outlet 24 of the chamber 14 is described in detail above. For purposes of simplification, the following description of the preferred embodiment of the method of the present invention will not make reference to the components of the apparatus 10 used to transport and apply the various fluids during the preferred steps of the method of the present invention. Instead, the method of the present invention will be discussed while only making reference to the application of fluids to either the proximal end 162 of the instrument 12 or to the exterior 32 of the instrument 12.

As further described below, the method of the present invention uses a driving fluid and, more particularly, pulses of the driving fluid of different duration to drive fluid, remove fluid, or to dry a portion of the instrument 12. It is preferable, but not necessary, that the driving fluid be air and that the air pulses be generated with a pressure of approximately seventy-five (75) pounds per square inch. Those having ordinary skill in the art will understand from the present disclosure that a driving fluid other than air, such as nitrogen or an inert fluid such as helium could be used without departing from the spirit and scope of the invention. For the purpose of disclosing the methods within the scope of this invention, hereafter, the term "air" will be used throughout to mean both an arbitrary driving fluid and also the preferred driving fluid with the understanding that the invention is not limited to the use of air as the driving fluid.

FIG. 11 illustrates one preferred method of the present invention that includes a plurality of steps, also referred to as cycles, and that takes approximately nine hundred twenty (920) seconds to complete. While a preferred order of steps is shown in FIG. 11, those of ordinary skill in the art will appreciate that the present invention is not limited to the specific order of steps disclosed. For example, Step 109, the third dry cycle, shown in FIG. 11 can be omitted without departing from the scope of the present invention. Additionally, those of ordinary skill in the art will appreciate from this disclosure that the timing and application of fluids for any one of the individual steps can be varied without departing from the scope of the present invention.

Referring to FIG. 11, step 101, the method of the present invention preferably, but not necessarily, includes a washing cycle 101 which washes the instrument 12 with a rinse fluid 46, such as sterilized water, to clean the exterior surface 32 and the proximal end 162 of the instrument 12. Those of ordinary skill in the art will appreciate from this disclosure that rinse fluids 46 other than sterilized water can be used without departing from the scope of the present invention.

The washing cycle preferably starts with injecting a pulse of the rinse fluid 46 onto the exterior 32 of the instrument 12. The pulse of rinse fluid 46 is injected onto the exterior 32 of the instrument 12 preferably for approximately one point twenty-five (1.25) seconds. After the pulse of the rinse fluid 46 is injected onto the exterior 32 of the instrument 12, a pulse of air is injected onto the exterior 32 of the instrument 12. The pulse of air is injected onto the exterior 32 of the instrument 12 preferably for approximately one point seventy-five (1.75) seconds to provide force to the rinse fluid 46 for aggressively washing the exterior 32 of the instrument 12. Then, a pulse of the rinse fluid 46 is preferably injected onto the proximal end 162 of the instrument 12 for one point twenty five (1.25) seconds, followed by the injection of a plurality of pulses of air onto the proximal end 162 of the instrument 12. The plurality, e.g., eight (8), of pulses of air are preferably injected in rapid succession to remove any rinse fluid 46 that could dilute the bio-burden removal fluid 48 (further described below). Those of ordinary skill in the art will appreciate from this disclosure that the rapid pulses of air can vary between two (2) and one hundred (100) or more without departing from the scope of the present invention. Each pulse of air is preferably, but not necessarily, slightly less than about zero point thirty-three (0.33) seconds in duration. Thus, allowing the time between the initiation of sequential pulses to preferably, but not necessarily, be about zero point thirty-three (0.33) seconds. The pulses of air provide force to the rinse fluid 46 to facilitate the cleaning of the instrument 12.

The above described application of the rinse fluid 46 to the exterior 32 and to the proximal end 162 of the instrument 12 is preferably repeated two additional times. While it is preferred that the wash cycle take approximately 20 seconds to complete, those of ordinary skill in the art will appreciate from this disclosure that the time of the wash cycle can be varied without departing from the scope of the present invention. While a preferred use of air pulses and the rinse fluid 46 to wash various portions of the instrument 12 has been described, those of ordinary skill in the art will appreciate from this disclosure that air and the rinse fluid 46 can be applied to the instrument 12 using different sequencing and timing while still washing the instrument 12 and without departing from the scope of the present invention.

Referring to FIG. 11, step 102, the method of the present invention preferably, but not necessarily, includes a first dry cycle 102 which dries various portions of the instrument 12. The first drying cycle 102 preferably lasts approximately five (5) seconds and comprises injecting a plurality of pulses of air onto the exterior 32 of the instrument 12 and injecting a plurality of pulses of air onto the proximal end 162 Of the instrument 12. Two (2) pulses of air are preferably injected onto the exterior 32 of the instrument 12. Then, two (2) pulses of air are preferably injected onto the proximal end 162 of the instrument 12 to remove any remaining rinse fluid 46. While it is preferred that the first drying cycle 102 take approximately five (5) seconds, those of ordinary skill in the art will appreciate from this disclosure that the time of the first drying cycle can be varied without departing from the scope of the present invention. While a preferred use of air pulses to dry various portions of the instrument 12 has been described, those of ordinary skill in the art will appreciate from this disclosure that air can be applied to the instrument 12 using a different sequencing and timing while still drying the instrument 12 and without departing from the scope of the present invention.

Referring to FIG. 11, step 103, the method of the present invention preferably, but not necessarily, includes removing bio-burden from the instrument 12 with a bio-burden removing fluid 48, such as a protease fluid. The bio-burden removing fluid 48 loosens and/or removes dried blood, saliva or the like on the instrument 12. Thus, the bio-burden removing step 103 attempts to expose pathogens which otherwise could be protected from the sterilizing fluid 50 by other biological matter that occludes the sterilizing fluid 50 from contact with pathogens.

The removing bio-burden step 103 preferably, but not necessarily, includes a first enzyme cycle and a second enzyme cycle. During the first enzyme cycle, a pulse of the bio-burden removing fluid 48, having a duration of preferably about two point five (2.5) seconds, is injected onto the exterior 32 of the instrument 12 followed by the injection of a pulse of air having a duration of preferably about two point five (2.5) seconds onto the exterior 32 of the instrument 12. While a preferred use of air pulses and the bio-burden removing fluid 48 to remove bio-burden from various portions of the instrument 12 has been described, those of ordinary skill in the art will appreciate from this disclosure that air and the bio-burden removing fluid 48 can be applied to the instrument 12 using a different sequencing and timing while still performing the first enzyme cycle and without departing from the scope of the present invention.

During the second enzyme cycle, the bio-burden removing fluid 48 is injected onto the proximal end 162 of the instrument 12 for preferably about zero point sixty-six (0.66) seconds, followed by the injection of a plurality of pulses of air onto the proximal end 162 of the instrument 12. The plurality, e.g., twelve (12), of pulses of air, each preferably about zero point seventeen (0.17) seconds in duration, are injected onto the proximal end 162 of the instrument 12 to provide force to any bio-burden removing fluid 48 disposed on the proximal end 162, or in the interior 28, of the instrument 12. The injection of the bio-burden removing fluid 48 onto the proximal end 162 of the instrument 12 and the plurality of pulses of air are preferably completed in about five (5) seconds. The injection of the bio-burden removing fluid 48 onto the proximal end 162 of the instrument 12 followed by the pulses of air is preferably repeated about five (5) more times during the second enzyme cycle. While it is preferred that the first and second enzyme cycles take approximately thirty-five (35) seconds, those of ordinary skill in the art will appreciate from this disclosure that the time of the first and second enzyme cycles can be varied without departing from the scope of the present invention.

Referring to FIG. 11, step 104, the method of the present invention preferably, but not necessarily, includes a first rinse cycle 104 which rinses the instrument 12 with the rinse fluid 46 for a duration of about ten (10) seconds. The first rinse cycle 104 starts with injecting the rinse fluid 46 onto the exterior 32 of the instrument 12 for preferably about one (1) second. Then, a pulse of air is injected onto the exterior 32 of the instrument 12 for preferably about two point five (2.5) seconds to remove the rinse fluid 46 from the instrument 12. Afterwards, a pulse of the rinse fluid 46 preferably is injected onto the proximal end 162 of the instrument 12 for approximately one (1) second. Once the rinse fluid 46 has been injected onto the proximal end 162 of the instrument 12, a plurality of pulses of air is injected onto the proximal end 162 of the instrument. The plurality, e.g., eight (8), of pulses of air are preferably injected in rapid succession, each pulse being approximately zero point thirty-three (0.33) seconds in duration, are injected onto the proximal end 162 of the instrument 12. Preferably, but not necessarily, the rinse fluid 46 again is injected into the chamber 14 and onto the exterior 32 of the instrument 12 for approximately one (1) second. The injection of the rinse fluid 46 is followed by a pulse of air that is directed into the chamber for approximately two point five (2.5) seconds to remove the rinse fluid 46 from the instrument 12.

While it is preferred that the first rinse cycle 104 take approximately ten (10) seconds, those of ordinary skill in the art will appreciate from this disclosure that the time of the first rinse cycle can be varied without departing from the scope of the present invention. While a preferred use of the rinse fluid 46 and air pulses has been described for completing the first rinse cycle 104, those of ordinary skill in the art will appreciate from this disclosure that air and the rinse fluid 46 can be applied to the instrument 12 using a different sequencing and timing while still rinsing the instrument 12 and without departing from the scope of the present invention.

Referring to FIG. 11, step 105, the method of the present invention preferably includes a second dry cycle 105 which dries various portions of the instrument 12. The second drying cycle 105 preferably has a duration of approximately ten (10) seconds and comprises injecting a plurality of pulses of air onto the exterior 32 of the instrument 12 and injecting a plurality of pulses of air onto the proximal end 162 of the instrument 12. Initially, two (2) pulses of air spaced apart in time and each having a duration of approximately zero point seven (0.7) seconds are injected into the chamber 14 and onto the exterior 32 of the instrument 12. Then, two (2) pulses of air spaced apart in time and each having a duration of about zero point seven (0.7) seconds are injected onto the proximal end 162 of the instrument 12. The injection of two (2) pulses of air into the chamber 14 and onto the proximal end 162 of the instrument is preferably repeated a second time. While it is preferred that the second dry cycle takes approximately ten (10) seconds, those of ordinary skill in the art will appreciate from this disclosure that the time of the second dry cycle can be varied without departing from the scope of the present invention. While a preferred use of air pulses has been described for completing the second dry cycle, those of ordinary skill in the art will appreciate from this disclosure that air can be applied to the instrument 12 using a different sequencing and timing while still drying the instrument 12 and without departing from the scope of the present invention.

Referring to FIG. 11, step 106, the method of the present invention preferably, but not necessarily, includes a temperature stabilization cycle 106 which stabilizes a sterilization temperature at which sterilization of the instrument 12 occurs. Preferably, the sterilizing temperature is maintained within a first range of about ninety-three degrees Fahrenheit to about ninety-seven degrees Fahrenheit. The stabilizing step 106 comprises maintaining the chamber at the sterilizing temperature during the first and second applications of the sterilizing fluid (discussed below) and maintaining the sterilizing fluid at the sterilizing temperature during the first and second applications of the sterilizing fluid. During the temperature stabilization cycle 106, the chamber temperature preferably is brought to between approximately ninety-three (93° F.) degrees Fahrenheit and approximately ninety-seven (97° F.) degrees Fahrenheit. By controlling the chamber temperature prior to initiating the use of the sterilizing fluid 50 and by controlling the temperature of the sterilizing fluid 50, the effectiveness of the sterilizing fluid 50 is increased. While it is preferred that the temperature stabilization cycle take approximately ninety (90) seconds, those of ordinary skill in the art will appreciate from this disclosure that the time of the temperature stabilization cycle can be varied without departing from the scope of the present invention. Additionally, depending upon the temperature of the chamber 14 prior to the sterilization cycle, the temperature stabilization cycle can be omitted without departing from the scope of the present invention. Further, the temperature stabilization cycle can be performed at any time the chamber temperature falls outside of a predetermined temperature range.

Referring to FIG. 11, step 107, the method of the present invention includes a sterilization cycle 107 which comprises applying to the instrument 12 a first application of a sterilizing fluid 50 at a first predetermined flow rate and a second application of the sterilizing fluid 50 at a second predetermined flow rate. The first application of the sterilizing fluid 50 preferably is applied to the instrument 12 at a first predetermined flow rate of about two (2) milliliter per second and the second application of the sterilizing fluid 50 preferably is applied to the instrument 12 at a rate that is less than about one-tenth the first predetermined flow rate. Those of ordinary skill in the art will appreciate from this disclosure that the first predetermined flow rate can vary between one hundred (100) milliliter per minute and one hundred seventy milliliter per minute without departing from the scope of the present invention. The artisan will further understand that the preferred flow rates are dependent on such factors as the effectiveness of the sterilizing fluid 50 as an anti pathogen, the steps included in the sterilization process and the duration of the steps.

The first application comprises a first predetermined sequence of pulses of the sterilizing fluid 50 and air. Preferably, the first predetermined sequence of pulses comprises a first segment having a first pulse of the sterilizing fluid 50 and a first pulse of air and a second segment having a second pulse of the sterilizing fluid 50 and a plurality of pulses of air. The first pulse of the sterilizing fluid 50 is injected onto the exterior 32 of the instrument 12 for preferably about three (3) seconds. The first pulse of air is injected onto the exterior 32 of the instrument 12 for approximately two (2) seconds. The second pulse of the sterilizing fluid 50 is injected onto the proximal end 162 of the instrument 12 for approximately zero point twenty-five (0.25) seconds. The plurality of pulses of air preferably is forty-four (44) pulses of air, each approximately zero point seventeen (0.17) seconds in duration, and is injected onto the proximal end 162 of the instrument 12. The use of the first pulse of air and the plurality of pulses of air drives the sterilizing fluid 50 into violent turbulent flow patterns to aid in the aggressive sterilization of the instrument 12. The second segment of the predetermined sequence is preferably repeated about five (5) additional times.

The second application of the sterilizing fluid 50 comprises a plurality of pulses of the sterilizing fluid 50, preferably applied only to the proximal end 162 of the instrument 12. Preferably, the plurality of pulses of the sterilizing fluid 50 is injected onto the proximal end 162 of the instrument 12 without using any driving air pulses. This results in the sterilizing fluid 50 of the second application having a low velocity which facilitates continuous contact of the sterilizing fluid 50 with the proximal end 162 and/or the interior 28 of the instrument 12. The plurality of pulses of the sterilizing fluid 50 is preferably about twenty (20) pulses per minute. The second application of the sterilizing fluid 50 preferably takes about one hundred forty-seven (147) seconds to complete. The type of fluid contact between the surfaces of the instrument 12 and the plurality of pulses of the sterilizing fluid 50 results in more effective sterilization than using air driven sterilizing fluid 50 on the instrument 12. The combination of applying the first application of the sterilizing fluid 50 using driving air pulses and applying the second application of the sterilizing fluid 50 without using driving air pulses results in superior sterilization. One of the reasons for the effectiveness of the method of the invention is the different types of contact generated between the sterilizing fluid 50 and the surfaces of the instrument 12 during the first and second applications.

After the second application is completed, the sterilizing fluid 50 preferably is applied six (6) more times to the proximal end 162 of the instrument 12 in accordance with the second segment of the predetermined sequence of the first application discussed above.

The total time to complete the sterilization cycle 107 is preferably, but not necessarily, approximately three hundred thirty (330) seconds. While a preferred application of air pulses and the sterilizing fluid 50 to various portions of the instrument 12 have been described for completing the sterilization cycle 107, those of ordinary skill in the art will appreciate from this disclosure that air and the sterilizing fluid 50 can be applied to the instrument 12 using a different sequencing and timing while still sterilizing the instrument 12 and without departing from the scope of the present invention. The method of the present invention preferably includes a repetition of the sterilization cycle 107 at least one additional time.

While the method of the present invention preferably repeats the sterilization step 107 at least an additional time, those of ordinary skill in the art will appreciate that the method of the present invention can be used without repetition and that repeating the sterilization step 107 is merely preferred as a redundant safety check to ensure the total sterilization of the instrument. However, the instrument 12 is completely sterilized after the completion of the sterilization step 107.

Referring to FIG. 11, steps 108 and 109, a second rinse cycle 108 and a third drying cycle 109 are preferably included in the method of the present invention and are substantially the same as the first rinse cycle 104 and the second drying cycle 105. Accordingly, for brevity details regarding the second rinse cycle 108 and the third drying cycle 109 are not further discussed.

Those skilled in the art will appreciate that changes may be made to the above-described embodiment of the present invention without departing from the broad inventive concept thereof. Accordingly, the artisan will understood, therefore, that this invention is not limited to the particular embodiment disclosed, but is intended to cover all modifications which are within the spirit and scope of the present invention as defined by the appended claims

We claim:

1. A method of sterilizing an instrument in a chamber of a sterilizing apparatus, the instrument having an exterior and a proximal end, the method comprising:

applying to the instrument a first application of a sterilizing fluid at a first predetermined flow rate, the first application comprising a first predetermined sequence of pulses of the sterilizing fluid and a driving fluid; and applying to the instrument a second application of the sterilizing fluid at a second predetermined flow rate, the second application comprising a plurality of pulses of the sterilizing fluid.

2. The method according to claim 1, wherein the first predetermined sequence of pulses comprises a first segment and a second segment, the first segment comprising a pulse of sterilizing fluid and a pulse of the driving fluid, the pulse of the sterilizing fluid and the pulse of the driving fluid being injected onto the exterior of the instrument, the second segment comprising a pulse of the sterilizing fluid and a plurality of pulses of the driving fluid, the pulse of the sterilizing fluid and the plurality of pulses of the driving fluid being injected onto the proximal end of the instrument; and the second application is applied to the proximal end of the instrument.

3. The method according to claim 2, wherein the second segment is applied to the instrument a plurality of times.

4. The method according to claim 1, further comprising stabilizing a sterilization temperature at which sterilization of the instrument occurs, the stabilizing step comprising maintaining the sterilization temperature within a first range of about ninety-three degrees Fahrenheit to about ninety-seven degrees Fahrenheit by maintaining the chamber at the sterilization temperature during the first and second applications of the sterilizing fluid; and maintaining the sterilizing fluid at the sterilization temperature during the first and second applications of the sterilizing fluid.

5. The method claim according to claim 1, further comprising removing bio-burden from the instrument with a bio-burden removing fluid.

6. The method according to claim 5, wherein the removing bio-burden step comprises a first enzyme cycle and a second enzyme cycle, the first enzyme cycle comprising: injecting a pulse of the bio-burden removing fluid onto the exterior of the instrument, and injecting a pulse of the driving fluid onto the exterior of the instrument, the second enzyme cycle comprising: injecting a pulse of the bio-burden removing fluid onto the proximal end of the instrument, and injecting a plurality of pulses of the driving fluid onto the proximal end of the instrument.

7. The method according to claim 1, further comprising:
removing bio-burden from the instrument with a bio-burden removing fluid;
stabilizing a sterilization temperature at which sterilization of the instrument occurs; and
a first rinsing of the instrument comprising: injecting a rinse fluid onto the exterior of the instrument; driving the rinse fluid against the exterior by injecting the driving fluid onto the exterior; injecting the rinse fluid onto the proximal end of the instrument; and injecting a plurality of pulses of the driving fluid onto the proximal end of the instrument.

8. A method of sterilizing an instrument in a chamber of a sterilizing apparatus, the instrument having an exterior and a proximal end, the method comprising:
washing the instrument with a rinse fluid;
removing bio-burden from the instrument with a bio-burden removing fluid;
stabilizing a sterilization temperature at which sterilization of the instrument occurs;
sterilizing the instrument, the sterilizing step comprising: applying to the instrument a first application of a sterilizing fluid at a first predetermined flow rate and applying to the instrument a second application of the sterilizing fluid at a second predetermined flow rate, the first application comprising a first predetermined sequence of pulses of the sterilizing fluid and a driving fluid, the second application comprising a plurality of pulses of the sterilizing fluid;

a first rinsing of the instrument with the rinse fluid; and a first drying of the instrument.

9. The method according to claim 8, wherein the washing step comprises: injecting a pulse of the rinse fluid onto the exterior of the instrument; injecting a pulse of the driving fluid onto the exterior of the instrument; injecting a pulse of the rinse fluid onto the proximal end of the instrument; and injecting a plurality of pulses of the driving fluid onto the proximal end of the instrument; and the first drying step comprises: injecting a plurality of pulses of the driving fluid onto the exterior of the instrument; and injecting a plurality of pulses of the driving fluid onto the proximal end of the instrument.

10. The method according to claim 8, wherein the removing bio-burden step comprises a first enzyme cycle and a second enzyme cycle, the first enzyme cycle comprising: injecting a pulse of the bio-burden removing fluid onto the exterior of the instrument, and injecting a pulse of the driving fluid onto the exterior of the instrument, the second enzyme cycle comprising: injecting a pulse of the bio-burden removing fluid onto the proximal end of the instrument, and injecting a plurality of pulses of the driving fluid onto the proximal end of the instrument;

the first predetermined sequence of pulses comprises a first segment and a second segment, the first segment comprising a pulse of the sterilizing fluid and a pulse of the driving fluid, the pulse of the sterilizing fluid and the pulse of the driving fluid being injected onto the exterior of the instrument, the second segment comprising a pulse of the sterilizing fluid and a plurality of pulses of the driving fluid, the pulse of the sterilizing fluid and the plurality of pulses of the driving fluid being injected onto the proximal end of the instrument; and the first rinsing step comprises: injecting the rinse fluid onto the exterior of the instrument; driving the rinse fluid against the exterior of the instrumentby injecting the driving fluid onto the exterior; injecting the rinse fluid onto the proximal end of the instrument, and injecting a plurality of pulses of the driving fluid onto the proximal end of the instrument.

11. A method of sterilizing an instrument in a chamber of a sterilizing apparatus, the instrument having an exterior and a proximal end, the method comprising:

washing the instrument with a rinse fluid;

a first drying of the instrument;

removing bio-burden from the instrument with a bio-burden removing fluid;

a first rinsing of the instrument with the rinse fluid;

a second drying of the instrument;

stabilizing a sterilization temperature at which sterilization of the instrument occurs;

sterilizing the instrument, the sterilizing step comprising applying to the instrument a first application of a sterilizing fluid at a first predetermined flow rate and applying to the instrument a second application of the sterilizing fluid at a second predetermined flow rate, the first application comprising a first predetermined sequence of pulses comprising the sterilizing fluid and a driving fluid, the second application comprising a plurality of pulses of the sterilizing fluid;

a second rinsing of the instrument with the rinse fluid; and a third drying of the instrument.

12. The method according to claim 11, wherein the washing step comprises: injecting a pulse of the rinse fluid onto the exterior of the instrument, injecting a pulse of the driving fluid onto the exterior of the instrument, injecting a pulse of the rinse fluid onto the proximal end of the instrument and injecting a plurality of pulses of the driving fluid onto the proximal end of the instrument;

the first, second and third drying steps comprise injecting a plurality of pulses of the driving fluid onto the exterior of the instrument, and injecting a plurality of pulses of the driving fluid onto the proximal end of the instrument;

the removing bio-burden step comprises a first enzyme cycle and a second enzyme cycle, the first enzyme cycle comprising: injecting a pulse of the bio-burden removing fluid onto the exterior of the instrument, and injecting a pulse of the driving fluid onto the exterior of the instrument, the second enzyme cycle comprising: injecting a pulse of the bio-burden removing fluid onto the proximal end of the instrument, and injecting a plurality of pulses of the driving fluid onto the proximal end of the instrument;

the first and second rinsing steps comprise: injecting the rinse fluid onto the exterior of the instrument; driving the rinse fluid against the exterior of the instrument by injecting the driving fluid onto the exterior; injecting the rinse fluid onto the proximal end of the instrument, and injecting a plurality of pulses of the driving fluid onto the proximal end of the instrument;

the stabilizing step comprises: maintaining the sterilization temperature within a first range of about ninety-three degrees Fahrenheit to about ninety-seven degrees Fahrenheit by maintaining the chamber at the sterilization temperature during the first and second applications of the sterilizing fluid; and maintaining the sterilizing fluid at the sterilization temperature during the first and second applications of the sterilizing fluid;

the first predetermined sequence of pulses comprises a first segment and a second segment, the first segment comprising a pulse of the sterilizing fluid and a pulse of the driving fluid, the pulse of the sterilizing fluid and the pulse of the driving fluid being injected onto the exterior of the instrument, the second segment comprising a pulse of the sterilizing fluid and a plurality of pulses of the driving fluid, the pulse of sterilizing fluid and the plurality of pulses of driving fluid being injected onto the proximal end of the instrument; and the second application is injected onto the proximal end of the instrument.

* * * * *